United States Patent
Leoni

(10) Patent No.: US 7,157,551 B2
(45) Date of Patent: Jan. 2, 2007

(54) COMPOSITIONS AND METHODS FOR THE DETECTION AND TREATMENT OF METHYLTHIOADENOSINE PHOSPHORYLASE DEFICIENT CANCERS

(75) Inventor: Lorenzo M. Leoni, San Diego, CA (US)

(73) Assignee: Cephalon, Inc., Frazer, PA (US)

( * ) Notice: Subject to any disclaimer, the term of this patent is extended or adjusted under 35 U.S.C. 154(b) by 0 days.

(21) Appl. No.: 10/779,476

(22) Filed: Feb. 13, 2004

(65) Prior Publication Data

US 2004/0247600 A1     Dec. 9, 2004

Related U.S. Application Data

(60) Provisional application No. 60/460,715, filed on Apr. 4, 2003, provisional application No. 60/447,888, filed on Feb. 14, 2003.

(51) Int. Cl.
*C07K 16/00* (2006.01)
*C07K 16/18* (2006.01)

(52) U.S. Cl. .................. 530/187.1; 530/388.1
(58) Field of Classification Search ............. 530/387.1, 530/350, 388.1
See application file for complete search history.

(56) References Cited

U.S. PATENT DOCUMENTS

| | | | |
|---|---|---|---|
| 4,366,241 A | 12/1982 | Tom et al. ...................... | 435/7 |
| 4,376,110 A | 3/1983 | David et al. ................ | 436/513 |
| 4,517,288 A | 5/1985 | Giegel et al. .................. | 435/7 |
| 4,569,788 A * | 2/1986 | Mulshine et al. .......... | 435/7.23 |
| 4,837,168 A | 6/1989 | de Jaeger et al. | |
| 5,744,585 A * | 4/1998 | Medenica et al. ..... | 530/388.15 |
| 5,840,505 A | 11/1998 | Carrera et al. ................ | 435/18 |
| 5,942,393 A | 8/1999 | Nobori et al. .................. | 435/6 |
| 6,210,917 B1 | 4/2001 | Carson et al. ................ | 435/18 |
| 6,214,571 B1 | 4/2001 | Carrera et al. ................ | 435/18 |
| 2004/0096436 A1* | 5/2004 | Carson et al. ............. | 424/94.4 |

FOREIGN PATENT DOCUMENTS

| | | |
|---|---|---|
| WO | WO 95/17908 | 7/1995 |
| WO | WO 9518233 | 7/1995 |
| WO | WO 99/67634 | 12/1999 |

OTHER PUBLICATIONS

Neil S. Greenspan and Enrico Di Cera, Defining epitopes: It's not as easy as it seems Nature Biotechnology vol. 17, p. 936-937, Oct. 1999.*

Garcia-Castellano, J.M., et al., Methylthioadenosine Phosphorylase Gene Deletions Are Common in Osteosarcoma, *Clinical Cancer Research*, 8(3):782-787 (2002).

Norobi, T., et al., Genomic Cloning of Methylthioadenosine Phosphorylase: A Purine Metabolic Enzyme Deficient in Multiple Different Cancers, *Proc. Natl. Acad. Sci, USA*, 93(6):6303-6208 (*1996).

Nobori, T., et al., Absence of Methylthioadenosine Phosphorylase in Human Gliomas, *Cancer Research*, 51(6):3193-3197 (1991).

Ragione, F.D., et al., Physicochemical and Immunological Studies on Mammalian 5'-Deoxy-5'-methylthioadenosine Phosphorylase, *The Journal of Biological Chemistry*, 265(11):6241-4246 (1990).

Tanimoto, T., et al., Evaluation of Antibodies Reactive with Porcine Lymphocytes and Lymphoma Cells in Formaliin-Fixed, Paraffin-Embedded, Antigen-Retrieved Tissue Sections, AJVR, 57(6):853-859 (1996).

Cairns, P., et al., Frequency of homozygous deletion at p16/CDKN2 in primary human tumours, *Nature Genetics*, 11:210-12 (1995).

Carrera, C.J., et al., Toxicity of L-alanosine to MTAP-deficient cells: Selective treatment strategy for cancer with CDKN2 deletion, *Proceedings of the American Association for Cancer Research*, vol. 37, Abstract No. 2775 (1996).

Chen, Z.H., et al., Expression of methylthioadenosine phosphorylase cDNA in p16, MTAP malignant cells: restoration of methylthioadenosine phosphorylase-dependent salvage pathways and alterations of sensitivity to inhibitors of purine *de novo* synthesis, *Molecular Pharmacology*, 52:903-911 (1997).

Christopher, S.A., et al., Methylthioadenosine phosphorylase, a gene frequently codeleted with p16cdkN2a/ARF, acts as a tumor supressor in a breast cancer cell line, *Cancer Research*, 62:6639-6644 (2002).

Efferth, T., et al., Methylthioadenosine phosphorylase as target to chemoselective treatment of T-cell acute lymphoblastic leukemic cells, *Blood Cells, Molecules and Disease*, 28(1):47-56 (2002).

Fitchen, J.H., et al., Methylthioadenosine phosphorylase deficiency in human leukemias and solid tumors, *Cancer Research*, 46:5409-5412 (1986).

Hannon, G.J., et al., p15INK4B is a potential effector of TGF-β-induced cell cycle arrest, *Nature*, 371:257-261 (1994).

(Continued)

*Primary Examiner*—Jeffrey Siew
*Assistant Examiner*—Lei Yao
(74) *Attorney, Agent, or Firm*—Pillsbury Winthrop Shaw Pittman LLP

(57) ABSTRACT

Compositions and methods involving agents that specifically bind to methylthioadenosine phosphorylase (MTAP) protein are disclosed. Illustrative compositions comprise binding agents that bind to human MTAP protein in biological samples, including embedded samples. The binding agents are useful, for example, in the detection, prognosis, and/or treatment of MTAP deficient cancers. Also disclosed are kits containing the reagents necessary for the detection of human MTAP protein in an embedded sample.

5 Claims, 2 Drawing Sheets

OTHER PUBLICATIONS

Harasawa, H., et al., Chemotherapy targeting methylthioadenosine phosphorylase (MTAP) deficiency in adult T cell leukemia (ATL), *Leukemia*, 16:1799-1807 (2002).

von Heyningen, V., Ranking antibody affinities, *Methods in Enzymology*, 121:472-481 (1986).

Houghten, R.A., General method for the rapid solid-phase synthesis of large numbers of peptides: Specificity of antigen—antibody interaction at the level of individual amino acids, *Proc. Natl. Acad. Sci. USA*, 82(15):5131-5135 (1985).

Handbook of Immunochemical Staining Methods, 3rd Edition, T. Boenisch, ed., DAKO Corporation, Carpinteria, California, 2001, 68 pages, available at: http://www.ihe.com/books/dako_handbook.pdf.

Kamatani, N., et al., Selective killing of human malignant cell lines deficient in methylthioadenosine phosphorylase, a purine metabolic enzyme, *Proc. Natl. Acad. Sci. USA*, 78(2):1219-1223 (1981).

Kamb, A., et al., A cell cycle regulator potentially involved in genesis of many tumor types, *Science*, 264(5157):436-440 (1994).

Köhler, G., et al., Continuous cultures of fused cells secreting antibody of predefined specificity, *Nature*, 256:495-497 (1975).

Köhler, G., et al., Derivation of specific antibody-producing tissue culture and tumor lines by cell fusion, *Eur. J. Immunol.* 6:511-519 (1976).

Nobori, T., et al., Deletions of the cyclin-dependent kinase-4 inhibitor gene in multiple human cancers, *Nature* 368:753-756 (1994).

Nobori, T., et al., Methylthioadenosine phosphorylase deficiency in human non-small cell lung cancers, *Cancer Research*, 53:1098-1101 (1993).

Olopade, O.I., et al., Construction of a 2.8-megabase yeast artificial chromosome contig and cloning of the human methylthioadenosine phosphorylase gene from the tumor suppressor region on 9p21, *Proc. Natl. Acad. Sci. USA*, 92:6489-6493 (1995).

Qiu, X., et al., Identification and characterization of a C(K/R)TC motif as a common epitope present in all subtypes of hepatis B surface antigen, *J. Immunol.*, 156:3350-3356 (1996).

Ragione, F.D., et al., Purification and characterization of recombinant human 5'-methylthioadenosine phosphorylase: Definite identification of coding cDNA, *Biochemical and Biophysical Research Communications*, 223:514-519 (1996).

Schofield, K., et al., The cell adhesion molecule, E-cadherin, distinguishes mesothelial cells from carcinoma cells in fluids, *Cancer (Cancer Cythopathology)* 81 (5):293-298 (1997).

Toohey, J.I., et al., Methylthio group cleavage from methylthioadenosine. Description of an enzyme and its relationship to the methylthio requirement of certain cells in culture, *Biochemical and Biophysical Research Communications*, 78(4):1273-1280 (1977).

* cited by examiner

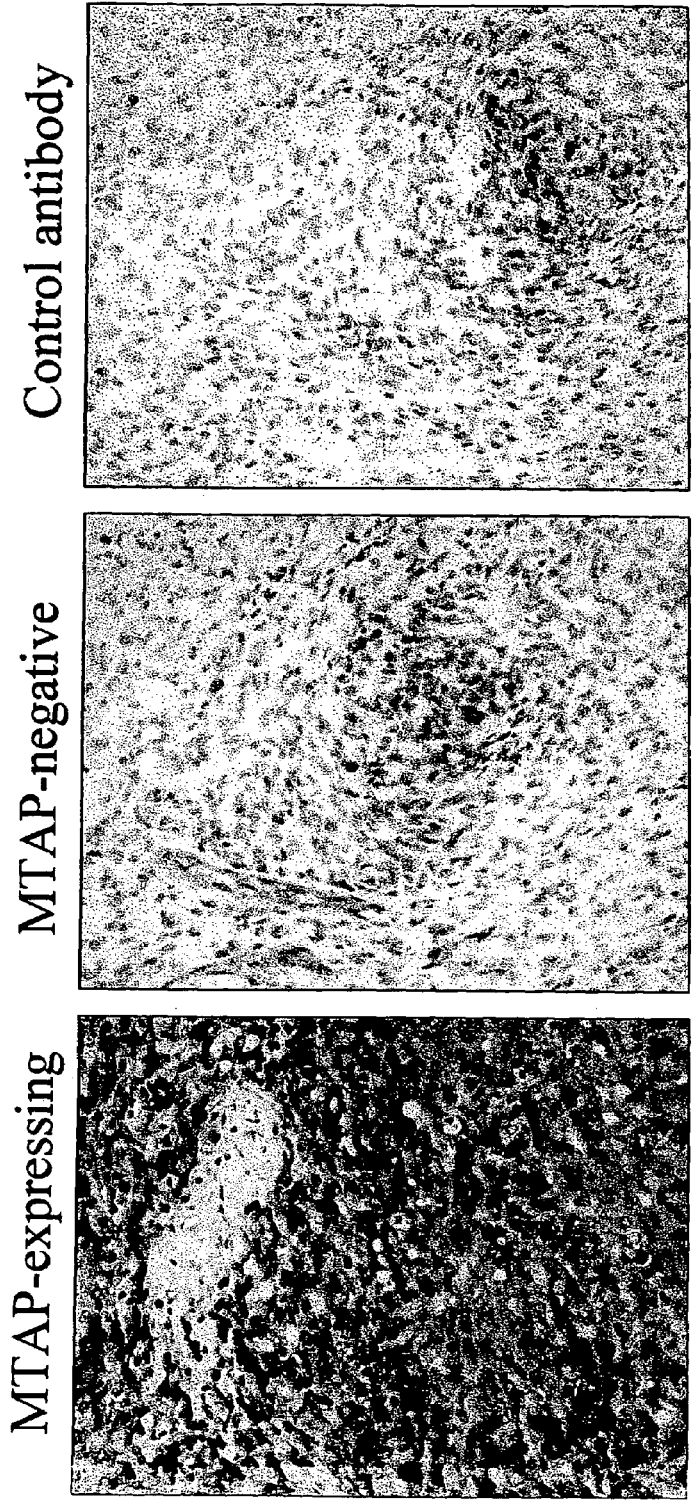

SEQUENCE LISTING

<160> NUMBER OF SEQ ID NOS: 12

<210> SEQ ID NO 1
<211> LENGTH: 283
<212> TYPE: PRT
<213> ORGANISM: Homo sapiens

<400> SEQUENCE: 1

```
Met Ala Ser Gly Thr Thr Thr Thr Ala Val Lys Ile Gly Ile Ile Gly
1               5                   10                  15

Gly Thr Gly Leu Asp Asp Pro Glu Ile Leu Glu Gly Arg Thr Glu Lys
            20                  25                  30

Tyr Val Asp Thr Pro Phe Gly Lys Pro Ser Asp Ala Leu Ile Leu Gly
        35                  40                  45

Lys Ile Lys Asn Val Asp Cys Ile Leu Leu Ala Arg His Gly Arg Gln
    50                  55                  60
```

```
His Thr Ile Met Pro Ser Lys Val Asn Tyr Gln Ala Asn Ile Trp Ala
 65                  70                  75                  80
Leu Lys Glu Glu Gly Cys Thr His Val Ile Val Thr Thr Ala Cys Gly
                 85                  90                  95
Ser Leu Arg Glu Glu Ile Gln Pro Gly Asp Ile Val Ile Asp Gln
            100                 105                 110
Phe Ile Asp Arg Thr Thr Met Arg Pro Gln Ser Phe Tyr Asp Gly Ser
            115                 120                 125
His Ser Cys Ala Arg Gly Val Cys His Ile Pro Met Ala Glu Pro Phe
            130                 135                 140
Cys Pro Lys Thr Arg Glu Val Leu Ile Glu Thr Ala Lys Lys Leu Gly
145                 150                 155                 160
Leu Arg Cys His Ser Lys Gly Thr Met Val Thr Ile Glu Gly Pro Arg
                165                 170                 175
Phe Ser Ser Arg Ala Glu Ser Phe Met Phe Arg Thr Trp Gly Ala Asp
            180                 185                 190
Val Ile Asn Met Thr Thr Val Pro Glu Val Val Leu Ala Lys Glu Ala
            195                 200                 205
Gly Ile Cys Tyr Ala Ser Ile Ala Met Ala Thr Asp Tyr Asp Cys Trp
            210                 215                 220
Lys Glu His Glu Glu Ala Val Ser Val Asp Arg Val Leu Lys Thr Leu
225                 230                 235                 240
Lys Glu Asn Ala Asn Lys Ala Lys Ser Leu Leu Thr Thr Ile Pro
                245                 250                 255
Gln Ile Gly Ser Thr Glu Trp Ser Glu Thr Leu His Asn Leu Lys Asn
            260                 265                 270
Met Ala Gln Phe Ser Val Leu Leu Pro Arg His
            275                 280
```

<210> SEQ ID NO 2
<211> LENGTH: 2269
<212> TYPE: DNA
<213> ORGANISM: Homo sapiens

<400> SEQUENCE: 2

```
gaattccgct ccgcactgct cactcccgcg cagtgaggtt ggcacagcca ccgctctgtg     60
gctcgcttgg ttcccttagt cccgagcgct cgcccactgc agattccttt cccgtgcaga    120
catggcctct ggcaccacca ccaccgccgt gaagattgga ataattggtg aacaggcct     180
ggatgatcca gaaattttag aaggaagaac tgaaaaatat gtggatactc catttggcaa    240
gccatctgat gccttaattt tggggaagat aaaaaatgtt gattgcatcc tccttgcaag    300
gcatggaagg cagcacacca tcatgccttc aaaggtcaac taccaggcga acatctgggc    360
tttgaaggaa gagggctgta cacatgtcat agtgaccaca gcttgtggct ccttgaggga    420
ggagattcag cccggcgata ttgtcattat tgatcagttc attgacagga ccactatgag    480
acctcagtcc ttctatgatg gaagtcattc ttgtgccaga ggagtgtgcc atattccaat    540
ggctgagccg ttttgcccca aaacgagaga ggttcttata gagactgcta agaagctagg    600
actccggtgc cactcaaagg ggacaatggt cacaatcgag ggacctcgtt ttagctcccg    660
ggcagaaagc ttcatgttcc gcacctgggg ggcggatgtt atcaacatga ccacagttcc    720
agaggtggtt cttgctaagg aggctggaat ttgttacgca agtatcgcca tggcgacaga    780
ttatgactgc tggaaggagc acgaggaagc agtttcggtg accgggtct aaagaccct     840
```

```
gaaagaaaac gctaataaag ccaaaagctt actgctcact accatacctc agatagggtc    900
cacagaatgg tcagaaaccc tccataacct gaagaatatg gcccagtttt ctgttttatt    960
accaagacat taaagtagca tggctgccca ggagaaaaga agacattcta attccagtca   1020
tttgggaat  tcctgcttaa cttgaaaaaa atatgggaaa gacatgcagc tttcatgccc   1080
ttgcctatca aagagtatgt tgtaagaaag acaagacatt gtgtgtatta gagactcctg   1140
aatgatttag acaacttcaa atacagaag  aaaagcaaat gactagtaaa catgtgggaa   1200
aaaatattac attttaaggg ggaaaaaaaa accccacca  ttctcttctc ccctattaa    1260
atttgcaaca ataaagggtg gagggtaatc tctactttcc tatactgcca aagaatgtga   1320
ggaagaaatg ggactctttg gttatttatt gatgcgactg taaattggta cagtatttct   1380
ggagggcaat ttggtaaaat gcatcaaaag acttaaaaat acggacgtcc tttggtgctg   1440
ggaactctac atctagcaat ttctctttaa accatatca  gagatgcata caagaatta    1500
tatataaga  agggtgttta ataatgatag ttataataat aaataattga acaatctga    1560
atcccttgca attggaggta aattatgtct tagttataat ctagattgtg aatcagccaa   1620
ctgaaaatcc ttttgcata  tttcaatgtc ctaaaaagac acggttgctc tatatatgaa   1680
gtgaaaaaag gatatggtag cattttatag tactagtttt gctttaaaat gctatgtaaa   1740
tatacaaaaa aactgaaaag aaatatatat aaccttgtta ttgtatttgg gggagggata   1800
ctgggataat ttttatttc  tttgaatctt tctgtgtctt cacatttttc tacagtgaat   1860
ataatcaaat agtaaagggc cgtaaaaata aaagtggatt tagaaagatc cagttcttga   1920
aaacactgtt tctggtaatg aagcagaatt taagttggta atattaaggt gaatgtcatt   1980
taagggagtt acatctttat tctgctaaag aagaggatca ttgatttctg tacagtcaga   2040
acagtacttg ggtgtgcaac agctttctga gaaaagctag gtgtataata gtttaactga   2100
aagtttaact atttaaaaga ctaaatgcac attttatggt atctgatatt ttaaaaagta   2160
atgtgagctt ctccttttta tgagttaaat tatttatac  gagttggtaa tttgtgcctt   2220
ttaataaagt ggaagcttgc ttttaaaaa  aaaaaaaaa  gcggaattc             2269
```

<210> SEQ ID NO 3
<211> LENGTH: 156
<212> TYPE: PRT
<213> ORGANISM: Homo sapiens

<400> SEQUENCE: 3

```
Met Glu Pro Ala Ala Gly Ser Ser Met Glu Pro Ser Ala Asp Trp Leu
1               5                   10                  15

Ala Thr Ala Ala Ala Arg Gly Arg Val Glu Glu Val Arg Ala Leu Leu
            20                  25                  30

Glu Ala Gly Ala Leu Pro Asn Ala Pro Asn Ser Tyr Gly Arg Arg Pro
        35                  40                  45

Ile Gln Val Met Met Met Gly Ser Ala Arg Val Ala Glu Leu Leu Leu
    50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
            100                 105                 110

Leu Pro Val Asp Leu Ala Glu Glu Leu Gly His Arg Asp Val Ala Arg
        115                 120                 125
```

```
Tyr Leu Arg Ala Ala Ala Gly Gly Thr Arg Gly Ser Asn His Ala Arg
    130                 135                 140

Ile Asp Ala Ala Glu Gly Pro Ser Asp Ile Pro Asp
145                 150                 155
```

<210> SEQ ID NO 4
<211> LENGTH: 1218
<212> TYPE: DNA
<213> ORGANISM: Homo sapiens

<400> SEQUENCE: 4

```
cccaacctgg ggcgacttca ggtgtgccac attcgctaag tgctcggagt taatagcacc    60
tcctccgagc actcgctcac ggcgtcccct tgcctggaaa gataccgcgg tccctccaga   120
ggatttgagg gacagggtcg gagggggctc ttccgccagc accggaggaa gaaagaggag   180
gggctggctg gtcaccagag ggtggggcgg accgcgtgcg ctcggcggct gcggagaggg   240
ggagagcagg cagcgggcgg cggggagcag catggagccg gcggcgggga gcagcatgga   300
gccttcggct gactggctgg ccacggccgc ggcccgggt cggtagagg aggtgcgggc    360
gctgctggag gcggggcgc tgcccaacgc accgaatagt tacggtcgga ggccgatcca   420
ggtcatgatg atgggcagcg cccgagtggc ggagctgctg ctgctccacg cgcggagcc    480
caactgcgcc gaccccgcca ctctcacccg accgtgcac gacgctgccc gggagggctt   540
cctggacacg ctggtggtgc tgcaccgggc cggggcgcgg ctggacgtgc gcatgcctg    600
gggccgtctg cccgtggacc tggctgagga gctgggccat cgcgatgtcg cacggtacct   660
gcgcgcggct gcggggggca ccagaggcag taaccatgcc cgcatagatg ccgcggaagg   720
tccctcagac atccccgatt gaagaaccca gagaggctct gagaaacctc gggaaactta   780
gatcatcagt caccgaaggt cctacagggc cacaactgcc cccgccacaa cccaccccgc   840
tttcgtagtt tcatttaga aatagagct tttaaaaatg tcctgccttt taacgtagat     900
atatgccttc ccccactacc gtaaatgtcc atttatatca tttttttatat attcttataa   960
aaatgtaaaa aagaaaaaca ccgcttctgc cttttcactg tgttggagtt ttctggagtg  1020
agcactcacg ccctaagcgc acattcatgt gggcatttct tgcgagcctc gcagcctccg  1080
gaagctgtcg acttcatgac aagcattttg tgaactaggg aagctcaggg gggttactgg  1140
cttctcttga gtcacactgc tagcaaatgg cagaaccaaa gctcaaataa aaataaaata  1200
attttcattc attcactc                                                1218
```

<210> SEQ ID NO 5
<211> LENGTH: 173
<212> TYPE: PRT
<213> ORGANISM: Homo sapiens

<400> SEQUENCE: 5

```
Met Gly Arg Gly Arg Cys Val Gly Pro Ser Leu Gln Leu Arg Gly Gln
1               5                   10                  15

Glu Trp Arg Cys Ser Pro Leu Val Pro Lys Gly Gly Ala Ala Ala
            20                  25                  30

Glu Leu Gly Pro Gly Gly Gly Glu Asn Met Val Arg Arg Phe Leu Val
        35                  40                  45

Thr Leu Arg Ile Arg Arg Ala Cys Gly Pro Pro Arg Val Arg Val Phe
    50                  55                  60

Val Val His Ile Pro Arg Leu Thr Gly Glu Trp Ala Ala Pro Gly Ala
65                  70                  75                  80
```

Pro Ala Ala Val Ala Leu Val Leu Met Leu Leu Arg Ser Gln Arg Leu
                85                  90                  95

Gly Gln Gln Pro Leu Pro Arg Arg Pro Gly His Asp Asp Gly Gln Arg
            100                 105                 110

Pro Ser Gly Gly Ala Ala Ala Pro Arg Arg Gly Ala Gln Leu Arg
        115                 120                 125

Arg Pro Arg His Ser His Pro Thr Arg Ala Arg Cys Pro Gly Gly
    130                 135                 140

Leu Pro Gly His Ala Gly Gly Ala Ala Pro Gly Arg Gly Ala Ala Gly
145                 150                 155                 160

Arg Ala Arg Cys Leu Gly Pro Ser Ala Arg Gly Pro Gly
                165                 170

<210> SEQ ID NO 6
<211> LENGTH: 1275
<212> TYPE: DNA
<213> ORGANISM: Homo sapien

<400> SEQUENCE: 6

```
cctccctacg ggcgcctccg gcagcccttc ccgcgtgcgc agggctcaga gccgttccga      60
gatcttggag gtccgggtgg gagtgggggt ggggtgggggg tggggtgaa ggtgggggggc    120
gggcgcgctc agggaaggcg ggtgcgcgcc tgcggggcgc agatgggcag ggggcggtgc    180
gtgggtccca gtctgcagtt aaggggggcag gagtggcgct gctcacctct ggtgccaaag    240
ggcggcgcag cggctgccga gctcggccct ggaggcggcg agaacatggt gcgcaggttc    300
ttggtgaccc tccggattcg gcgcgcgtgc ggcccgccgc gagtgagggt tttcgtggtt    360
cacatcccgc ggctcacggg ggagtgggca gcgccagggg cgcccgccgc tgtggccctc    420
gtgctgatgc tactgaggag ccagcgtcta gggcagcagc cgcttcctag aagaccaggt    480
catgatgatg ggcagcgccc gagtggcgga gctgctgctg ctccacggcg cggagcccaa    540
ctgcgccgac cccgccactc tcacccgacc cgtgcacgac gctgcccggg agggcttcct    600
ggacacgctg gtggtgctgc accgggccgg ggcgcggctg gacgtgcgcg atgcctgggg    660
ccgtctgccc gtggacctgg ctgaggagct gggccatcgc gatgtcgcac ggtacctgcg    720
cgcggctgcg gggggcacca gaggcagtaa ccatgcccgc atagatgccg cggaaggtcc    780
ctcagacatc cccgattgaa agaaccagag aggctctgag aaacctcggg aaacttagat    840
catcagtcac cgaaggtcct acagggccac aactgcccccc gccacaaccc accccgcttt    900
cgtagttttc atttagaaaa tagagctttt aaaaatgtcc tgccttttaa cgtagatata    960
tgccttcccc cactaccgta aatgtccatt tatatcattt tttatatatt cttataaaaa   1020
tgtaaaaaag aaaaacaccg cttctgcctt ttcactgtgt tggagttttc tggagtgagc   1080
actcacgccc taagcgcaca ttcatgtggg catttcttgc gagcctcgca gcctccggaa   1140
gctgtcgact tcatgacaag catttttgtga actagggaag ctcaggggggg ttactggctt   1200
ctcttgagtc acactgctag caaatggcag aaccaaagct caaataaaaa taaataatt   1260
ttcattcatt cactc                                                   1275
```

<210> SEQ ID NO 7
<211> LENGTH: 105
<212> TYPE: PRT
<213> ORGANISM: Homo sapiens

<400> SEQUENCE: 7

```
Met Met Met Gly Ser Ala Arg Val Ala Glu Leu Leu Leu His Gly
1               5                   10                  15

Ala Glu Pro Asn Cys Ala Asp Pro Ala Thr Leu Thr Arg Pro Val His
                20                  25                  30

Asp Ala Ala Arg Glu Gly Phe Leu Asp Thr Leu Val Val Leu His Arg
            35                  40                  45

Ala Gly Ala Arg Leu Asp Val Arg Asp Ala Trp Gly Arg Leu Pro Val
        50                  55                  60

Asp Leu Ala Glu Glu Leu Gly His Arg Asp Val Ala Arg Tyr Leu Arg
65                  70                  75                  80

Ala Ala Ala Gly Gly Thr Arg Gly Ser Asn His Ala Arg Ile Asp Ala
                85                  90                  95

Ala Glu Gly Pro Ser Asp Ile Pro Asp
            100                 105
```

<210> SEQ ID NO 8
<211> LENGTH: 897
<212> TYPE: DNA
<213> ORGANISM: Homo sapiens

<400> SEQUENCE: 8

```
tgtgtggggg tctgcttggc ggtgaggggg ctctacacaa gcttcctttc cgtcatgccg    60
gcccccaccc tggctctgac cattctgttc tctctggcag gtcatgatga tgggcagcgc   120
ccgagtggcg gagctgctgc tgctccacgg cgcggagccc aactgcgccg accccgccac   180
tctcacccga cccgtgcacg acgctgcccg ggagggcttc ctggacacgc tggtggtgct   240
gcaccgggcc ggggcgcggc tggacgtgcg cgatgcctgg ggccgtctgc ccgtggacct   300
ggctgaggag ctgggccatc gcgatgtcgc acggtacctg cgcgcggctg cggggggcac   360
cagaggcagt aaccatgccc gcatagatgc cgcggaaggt ccctcagaca tccccgattg   420
aaagaaccag agaggctctg agaaacctcg ggaaacttag atcatcagtc accgaaggtc   480
ctacagggcc acaactgccc ccgccacaac ccaccccgct ttcgtagttt tcatttagaa   540
aatagagctt ttaaaaatgt cctgcctttt aacgtagata taagccttcc cccactaccg   600
taaatgtcca tttatatcat ttttatata ttcttataaa aatgtaaaaa agaaaaacac   660
cgcttctgcc ttttcactgt gttggagttt tctggagtga gcactcacgc cctaagcgca   720
cattcatgtg ggcatttctt gcgagcctcg cagcctccgg aagctgtcga cttcatgaca   780
agcattttgt gaactaggga agctcagggg ggttactggc ttctcttgag tcacactgct   840
agcaaatggc agaaccaaag ctcaaataaa ataaaataa ttttcattca ttcactc       897
```

<210> SEQ ID NO 9
<211> LENGTH: 116
<212> TYPE: PRT
<213> ORGANISM: Homo sapiens

<400> SEQUENCE: 9

```
Met Glu Pro Ala Ala Gly Ser Ser Met Glu Pro Ser Ala Asp Trp Leu
1               5                   10                  15

Ala Thr Ala Ala Ala Arg Gly Arg Val Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Gly Arg Arg Ser Ala Ala Gly Ala Gly Asp Gly Gly Arg
        50                  55                  60
```

```
Leu Trp Arg Thr Lys Phe Ala Gly Glu Leu Glu Ser Gly Ser Ala Ser
 65                 70                  75                  80
Ile Leu Arg Lys Lys Gly Arg Leu Pro Gly Glu Phe Ser Glu Gly Val
                85                  90                  95
Cys Asn His Arg Pro Pro Pro Gly Asp Ala Leu Gly Ala Trp Glu Thr
            100                 105                 110
Lys Glu Glu Glu
        115

<210> SEQ ID NO 10
<211> LENGTH: 1515
<212> TYPE: DNA
<213> ORGANISM: Homo sapiens

<400> SEQUENCE: 10
cccaacctgg ggcgacttca ggtgtgccac attcgctaag tgctcggagt taatagcacc      60
tcctccgagc actcgctcac ggcgtcccct tgcctggaaa gataccgcgg tccctccaga     120
ggatttgagg gacagggtcg gaggggggctc ttccgccagc accggaggaa gaaagaggag    180
gggctggctg gtcaccagag ggtggggcgg accgcgtgcg ctcggcggct gcggagaggg     240
ggagagcagg cagcgggcgg cggggagcag catggagccg gcgcggggga gcagcatgga     300
gccggcggcg gggagcagca tggagccttc ggctgactgg ctggccacgg ccgcggcccg     360
gggtcgggta gaggaggtgc gggcgctgct ggaggcgggg gcgctgccca acgcaccgaa     420
tagttacggt cggaggccga tccaggtggg tagaaggtct gcagcgggag caggggatgg     480
cgggcgactc tggaggacga agtttgcagg ggaattggaa tcaggtagcg cttcgattct     540
ccggaaaaag gggaggcttc ctggggagtt ttcagaaggg gtttgtaatc acagacctcc     600
tcctggcgac gccctggggg cttgggaaac caaggaagag gaatgaggag ccacgcgcgt     660
acagatctct cgaatgctga gaagatctga agggggggaac atatttgtat tagatggaag    720
tcatgatgat gggcagcgcc cgagtggcgg agctgctgct gctccacggc gcggagccca     780
actgcgccga ccccgccact ctcacccgac ccgtgcacga cgctgcccgg gagggcttcc     840
tggacacgct ggtggtgctg caccgggccg gggcgcggct ggacgtgcgc gatgcctggg     900
gccgtctgcc cgtggacctg gctgaggagc tgggccatcg cgatgtcgca cggtacctgc     960
gcgcggctgc ggggggcacc agaggcagta accatgcccg catagatgcc gcggaaggtc    1020
cctcagacat ccccgattga agaaccagga gaggctctga gaaacctcgg gaacttagat    1080
catcagtcac cgaaggtcct acagggccac aactgccccc gccacaaccc accccgcttt    1140
cgtagttttc atttagaaaa tagagctttt aaaaatgtcc tgcctttttaa cgtagatata    1200
tgccttcccc cactaccgta aatgtccatt tatatcattt tttatatatt cttataaaaa    1260
tgtaaaaaag aaaaacaccg cttctgcctt ttcactgtgt tggagttttc tggagtgagc    1320
actcacgccc taagcgcaca ttcatgtggg catttcttgc gagcctcgca gcctccggaa    1380
gctgtcgact tcatgacaag cattttgtga actagggaag ctcaggggggg ttactggctt    1440
ctcttgagtc acactgctag caaatggcag aaccaaagct caaataaaaa taaataatt     1500
ttcattcatt cactc                                                     1515

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Primer for
```

-continued

```
      cloning MTAP cDNA

<400> SEQUENCE: 11
ctcgcccact gcagattcct ttcccgt                                            27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Antisense
      primer for cloning MTAP cDNA

<400> SEQUENCE: 12
ggcagccatg ctactttaat gtcttgg                                            27
```

COMPOSITIONS AND METHODS FOR THE DETECTION AND TREATMENT OF METHYLTHIOADENOSINE PHOSPHORYLASE DEFICIENT CANCERS

CROSS REFERENCE TO RELATED APPLICATIONS

This application claims the benefit of U.S. Applications Nos. 60/460,715 (filed Apr. 4, 2003) and 60/447,888 (filed Feb. 14, 2003) both of which are incorporated herein by reference in their entireties including figures.

FIELD OF THE INVENTION

The invention comprises binding agents against human methylthioadenosine phosphorylase (MTAP) protein, and uses thereof in determining the presence or absence of MTAP protein in an embedded sample, the prognosis of cancers associated with deletions of the gene encoding for MTAP protein, and methods of treatment for such cancers.

BACKGROUND AND INTRODUCTION TO THE INVENTION

The following discussion describes certain art references, none of which is admitted to be prior art to the invention described herein.

Methylthioadenosine phosphorylase (MTAP) is an enzyme found in all normal tissues that catalyzes the conversion of methylthioadenosine (MTA) into adenine and 5-methylthioribose-1-phosphate. Afterward, the adenine is salvaged to generate adenosine monophosphate, and the 5-methylthioribose-1-phosphate is converted to methionine and formate. Because of this salvage pathway, MTA can serve as an alternative purine source if de novo purine synthesis is blocked, e.g., with antimetabolites, such as L-alanosine.

Many human and murine malignant cells lack MTAP activity. MTAP deficiency is not only found in tissue culture cells but the deficiency is also present in primary leukemias, gliomas, melanomas, pancreatic cancers, non-small cell lung cancers (NSLC), bladder cancers, astrocytomas, osteosarcomas, head and neck cancers, myxoid chondrosarcomas, ovarian cancers, endometirial cancers, breast cancers, soft tissue sarcomas, non-Hodgkin lymphomas, and mesotheliomas (Kamatani et al. (1981) *Proc. Natl. Acad. Sci USA* 78:1219–1223; Toohey (1977) *Biochem. Biophys. Res. Commun.* 78:1273–1280; Fitchen et al. (1986) *Cancer Res.* 46:5409–5412; Nobori et al. (1991) *Cancer Res.* 51:3193–3197; Nobori et al. (1993) *Cancer Res.* 53:1098–1101; Christopher et al. (2002) *Cancer Res.* 62:6639–6644; and Garcia-Castellano et al. (2002) *Clin. Cancer. Res.* 8:782–787). Homozygous deletion is frequently the mechanism for inactivation of the gene encoding MTAP (Christopher et al. (2002) *Cancer Research* 62:6639–6644). Other mechanisms for MTAP deficiency, however, have been reported (Harasawa et al. (2002) *Leukemia* 16:1799–1807).

The gene encoding for human MTAP maps to region 9p21 on human chromosome 9p. This region also contains the tumor suppressor genes $p16^{INK4A}$ (also know as CDKN2A), and $p15^{INK4B}$. These genes encode for p16 and p15, which are inhibitors of the cyclin D-dependent kinases cdk4 and cdk6, respectively (Efferth et al. (2002) *Blood, Cells, Molec., and Dis.* 28:47–56; Kamp et al.(1994) *Science* 264:436–440; Hannon et al. (1994), *Nature* 371:257–261). The $p16^{INK4A}$ transcript can be alternatively ARF ARF spliced into a transcript encoding $p14^{ARF}$. $p14^{ARF}$ binds to MDM2 and prevents degradation of p53 (Pomerantz et al. (1998) *Cell* 92:713–723).

The 9p21 chromosomal region is of interest because it is frequently homozygously deleted in a variety of cancers, including leukemias, NSLC, pancreatic cancers, gliomas, melanomas, and mesothelioma. The deletions often inactivate more than one gene. For example, Cairns et al. ((1995) *Nat. Gen.* 11:210–212) reported that after studying more than 500 primary tumors, almost all the deletions identified in such tumors involved a 170 kb region containing MTAP, $p14^{ARF}$ and $P16^{INK4A}$ Carson et al. (WO 99/67634) reported that a correlation exists between the stage of tumor development and loss of homozygosity of the gene encoding MTAP and the gene encoding p16. For example, deletion of the MTAP gene, but not $p16^{INK4A}$ was reported to be indicative of a cancer at an early stage of development, whereas deletion of the genes encoding for p16 and MTAP was reported to be indicative of a cancer at a more advanced stage of tumor development. Garcia-Castellano et al. reported that in some osteosarcoma patients, the MTAP gene was present at diagnosis but was deleted at a later time point (Garcia-Castellano et al., supra).

Reference protein sequences for p16 and alternative transcripts, including p14, are deposited in GenBank under the following accession numbers NP_000068; NP_478102.1; NP_478103.1, and NP_478104.1. Reference mRNA sequences for p16 and alternative transcripts, including p14, are deposited in Genbank under accession numbers NM_000077.2; NM_058195.1; NM_058196.1; and NM_058197.1. Reference protein sequences for p15 are deposited under GenBank accession numbers NP_004927.2 and NP_511042.1. Reference mRNA sequences for p15 are deposited in GenBank under accession numbers NM_004936.2 and NM_078487.1.

Methods for determining the MTAP status in tumor cells have been described. U.S. Pat. No. 5,942,393 is said to describe methods for detecting MTAP-encoding nucleic acid through use of oligonucleotide probes. Norbori et al. ((1991) *Cancer Res.* 51:3193–3197); and (1993) *Cancer Res.* 53:1098–1101) reported the use of a polyclonal antisera to bovine MTAP to detect MTAP protein isolated from tumor cell lines or primary tumor specimens in an immunoblot analysis. Garcia-Castellano et al. (2002, supra) report the use of antihuman MTAP chicken antibody to screen osteosarcoma tumor samples that were embedded in OCT frozen blocks.

Because many tumor cells are MTAP deficient and, therefore, dependent on de novo purine synthesis for growth and/or survival, the MTAP salvage pathway may offer an opportunity for selective tumor therapy which spares normal tissues. To this end, the development of therapies based on treating MTAP deficient cancers with chemotherapeutic regimens that interfere with purine utilization is presently underway. Thus, a need exists for compositions and methods that identify MTAP deficient tumors.

In particular, a need exists for compositions and methods that identify MTAP deficient tumors (tumor cells that produce no or low amounts of MTAP protein) in biological samples, particularly those biological samples commonly used in a medical environment, such as formalin-fixed paraffin-embedded (FFPE) tissue specimens. The ability to detect human MTAP protein using immunohistochemistry techniques may be advantageous over other immunoassay techniques, such as Western blotting, as well as oligonucleotide based procedures, such as Southern blotting, in that individual cells can be screened and the chance of contaminating tumor cells with normal cells is reduced.

SUMMARY OF THE INVENTION

According to one aspect of the present invention, described herein are MTAP-binding agents that specifically bind to human methylthioadenosine phosphorylase (MTAP) protein and methods of their use.

In one embodiment, the invention is directed to MTAP-binding agents that bind to human MTAP in an embedded biological sample, including biological samples embedded in wax, nitrocellulose, polyethylene glycol, or plastic but not OCT compound. More preferred are MTAP-binding agents that bind to human MTAP protein in a biological sample embedded in paraffin. Even more preferred are MTAP-binding agents that bind to human MTAP in fixed biological samples embedded in paraffin. A preferred fixative is formalin. Preferred MTAP-binding agents are antibodies that specifically bind to human MTAP, including polyclonal and monoclonal antibodies. Especially preferred are anti-MTAP monoclonal antibodies. Preferably, the antibodies bind to human MTAP protein with an affinity greater than $10^5$ $M^{-1}$ and even more preferably with an affinity greater than $10^7$ $M^{-1}$.

In another embodiment, the invention is directed to the anti-MTAP monoclonal antibody produced by hybridoma cell line ATCC PTA-5001 and its use. In another aspect, the invention is directed to monoclonal antibodies that bind to the same epitope as the monoclonal antibodies produced by hybridoma cell line ATCC PTA-5001. In yet another aspect, the invention is directed to the hybridoma cell lines that produce anti-MTAP monoclonal antibodies.

According to one aspect, the present invention is directed to a monoclonal antibody which is capable of binding human MTAP protein in an embedded biological sample wherein said biological sample is not embedded in OCT compound. According to one feature of this aspect, the monoclonal antibody binds to the same human MTAP epitope as the monoclonal antibody produced by a cell line having ATCC Accession No. PTA-5001.

According to an alternate aspect, the present invention is directed to a monoclonal antibody secreted by a cell line deposited by ATCC Accession No. PTA-5001.

According to a further aspect, the present invention is directed to functional antigen binding fragments of a monoclonal antibody secreted by the cell line having ATCC Accession No. PTA-5001.

According to another aspect, the present invention is directed to functional antigen binding fragments of a monoclonal antibody which binds to the same human MTAP epitope as a monoclonal antibody produced by a cell line having ATCC Accession No. PTA-5001.

In still another embodiment, the invention is directed to a method of making an isolated hybridoma that produces an antibody useful for assessing whether an embedded biological sample includes cells that contain human MTAP protein. This method involves the following steps: (1) immunizing a mammal using a composition including a human MTAP polypeptide; (2) isolating splenocytes from the immunized mammal and fusing the isolated splenocytes with an immortalized cell to form hybridomas; and (3) screening the hybridomas for those that produce an antibody that specifically binds with human MTAP protein in an embedded biological sample.

In yet another embodiment, the invention is directed to a method for detecting the presence or absence of human MTAP protein in an embedded biological sample, including samples embedded in wax, nitrocellulose, PEG, or plastic. One disclosed method involves the following steps: (1) contacting the embedded biological sample with an MTAP-binding agent that forms a binding complex with human MTAP protein if present in the sample; and (2) detecting, using methods described herein, the quantity of binding complex formed. Detection of little to no binding complex is indicative of little or no human MTAP protein in the biological sample. Preferably, the sample is embedded in paraffin. Even more preferably, the sample is fixed. Preferably, the fixative is formalin. Methods for detecting the binding complex include labeling the binding agent with a detectable marker. In another aspect, the binding agent, contained in the binding complex, can be detected by using a detectably labeled second agent that binds to the binding agent. In yet another aspect, the binding agent, contained in the binding complex, can be detected using an unlabeled second agent that binds to the binding agent. The second agent can then be detected using a detectably labeled third agent that binds to the second agent.

Another method, disclosed herein, for detecting the presence or absence of human MTAP protein in a formalin-fixed paraffin embedded biological sample includes the following steps: (1) heating the sample to melt the paraffin; (2) deparaffinizing the sample, (3) inducing epitope retrieval in the sample, (4) incubating the sample with an MTAP-binding agent that specifically binds with human MTAP protein to form a binding complex; and (5) detecting the binding complex formed. Detection of little to no binding complex is indicative of little or no human MTAP protein in the sample. A preferred method for inducing epitope retrieval is through the use of heat. Another preferred method for epitope retrieval is heating followed by treatment with a proteolytic enzyme. A preferred proteolytic enzyme is trypsin.

In another embodiment, the invention is directed to methods of detecting the presence or absence of human MTAP protein in a sample including the following steps: (1) contacting the sample with a monoclonal antibody that specifically binds to human MTAP protein to form a binding complex; and (2) determining the presence or absence of binding complex in the sample, whereby the presence of the binding complex indicates the presence of human MTAP protein in the sample. A preferred monoclonal antibody is the monoclonal antibody produced by hybridoma cell line ATCC PTA-5001. Preferably, the method is an immunoassay such as a Western blot or ELISA assay.

In yet another embodiment, the invention is directed to an anti-human MTAP monoclonal antibody immobilized onto a solid surface.

In a further embodiment, the invention is directed to an MTAP-binding agent that specifically binds to human MTAP protein present in an embedded biological sample and yields a statistical score, based on staining intensities, that permits the identification of an embedded sample including cells homozygously deleted for the gene encoding human MTAP protein. Preferably the embedded sample is embedded in wax, nitrocellulose, PEG, or plastic. Preferred MTAP-binding agents for the method include antibodies. More preferred MTAP-binding agents for the method are monoclonal antibodies. Especially preferred are monoclonal antibodies produced by hybridoma cell line ATCC PTA-5001.

The methods disclosed herein can be used with embedded biological samples from patients with cancer. According to one aspect, the embedded sample is from a cancer that is selected from the group consisting of non-Hodgkin's lymphoma, mesothelioma, primary brain malignancies, (such as glioblastoma, glioma and astrocytoma), non-small cell lung cancer, leukemia, (such as acute lymphocytic leukemia, acute myelogenous leukemia, chronic lymphocytic leukemia, and chronic myelogenous leukemia), bladder cancer, pancreatic cancer, soft tissue sarcoma, osteosarcoma, or head and neck cancer. Preferably, the samples are fixed and embedded in paraffin.

Preferred MTAP-binding agents for use in the methods disclosed described herein are antibodies that specifically bind to human MTAP. Preferred are polyclonal or monoclonal antibodies that specifically bind to human MTAP. Preferable are antibodies that bind to human MTAP protein with an affinity greater than $10^5$ $M^{-1}$ and even more preferably with an affinity greater than $10^7$ $M^-$. A preferred anti-human MTAP monoclonal antibody for use in the methods disclosed herein are the monoclonal antibodies produced by hybridoma cell line ATCC PTA-5001, or monoclonal antibodies that bind to the same epitope as the monoclonal antibodies produced by hybridoma cell ATCC PTA-5001.

In another embodiment, the invention is directed to methods of selecting a patient for treatment of an MTAP deficient cancer with a therapy regimen directed to MTAP deficient cancers. A preferred method includes the following steps: (1) providing an embedded biological sample of the cancer from said patient; (2) contacting said sample with an MTAP-binding agent that specifically forms a binding complex with human MTAP protein present in the sample; and (3) detecting the quantity of binding complex, as described herein. Using this method, cancers with low or no detectable binding complex indicate cancers amenable to treatments directed to MTAP-deficient cancers. A preferred therapy regimen includes a drug that inhibits de novo purine synthesis. Preferred de novo purine syntheis inhibitors include L-alanosine, 10-propargyl-10-deazaminopterin (PDX), N-(4-(((2,4-diamino-6-pteridinyl)methyl)methylamino)benzoyl)-L-glutamic acid) (methotrexate), AG2037 (Agouron/Pfizer), 4-aminopteroylglutamic acid (aminopterin), 2,4-diamino-5-methyl-6-[[(3,4,5-trimethoxyphenyl)amino]methyl]quinazoline (trimetrexate), pyritrexim, 10-ethyl-deaza-aminopterin (edatrexate), 4'-methylene-10-deazaminopterin (MDAM), 10-propargyl-5,8-dideazafolic acid (PDDF), N-[5-[N-(3,4-dihydro-2-methyl-4-oxo-quinazolin-6-ylmethyl)-N-methylamino]-2-thenoyl-L-glutamic acid (raltitrexed; ZD1694, Tomudex), N-[4-[2-(2-amino-3,4-dihydro-4-oxo-7H-pyrrolo[2,3-d]-pyrimidin-5-yl)ethyl]-benzoyl]-L-glutamic acid (LY231514; Lilly), 6-(2'-formyl-2'naphthyl-ethyl)-2-amino-4(3H)-oxoquinazoline (LL95509), (6R,S)-5,10-dideazatetrahydrofolic acid (DDATHF), 4-[2-(2-amino-4-oxo-4,6,7,8-tetrahydro-3Hpyrimidino[5,4,6][1,4]-thiazin-6yl)-(S)-ethyl]-2,5-thienoylamino-L-glutamic acid (AG2034), and N-[5-(2-[(2,6-diamino-4(3H)-oxopyrimidin-5-yl)thio]ethyl)thieno-2-yl]-L-glutamic acid (AG2009), 6R2',5'thienyl5,10-dideazatetrahydrofolic acid (LY309887), (S)-2-[4-[N-[(3,4-dihydro-2,7-dimethyl-4-oxo-6-quinazolinyl)methyl]-N-prop-2-ynylamino]-2-fluorob enzamido]-4-(1H-1,2,3,4-tetrazol-5-yl)butyric acid (ZD9331), N-[4-[N-[(3,4-dihydro-2,7-dimethyl-4-oxo-6-quinazolinyl)methyl]-N-prop-2-ynylamino]-2-fluorob enzoyl]-L-glutamic acid (ZM214888), N(alpha)-[4-[5-(2,4-diaminoteridin-6-yl)pent-1-yn-4-yl]benzoyl]-N(delta)-hemiphthaloyl-L-ornithine, or N(alpha)-(4-amino-4-deoxypteroyl)-N(delta)-hemiphthaloyl-L-ornithine (PT523). Suitable patients for screening according to these methods include patients with a non-Hodgkin's lymphoma, mesothelioma, primary brain malignancies, such as glioblastoma, glioma, and astrocytoma, non-small cell lung cancer, leukemia, such as ALL, AML, CLL and CML, bladder cancer, pancreatic cancer, soft tissue sarcoma, osteosarcoma, or head and neck cancer.

In yet another embodiment, the invention is directed to kits for determining whether an embedded biological sample contains human MTAP protein. A preferred kit includes an MTAP-binding agent that specifically binds with human MTAP protein to form a binding complex, and an indicator capable of signaling the formation of said binding complex. Preferred MTAP-binding agents included with the kits are antibodies, preferably polyclonal or monoclonal antibodies that specifically react with human MTAP. More preferred MTAP-binding agents are anti-MTAP monoclonal antibodies that are produced by hybridoma cell line ATCC PTA-5001 or a monoclonal antibody that recognizes the same epitope as the monoclonal antibody produced by hybridoma cell line ATCC PTA-5001.

Also disclosed herein are methods for determining the homozygous deletion of the MTAP gene complex in a biological sample comprising the steps of: (1) contacting the sample with a binding agent that specifically binds to human MTAP protein to form a binding complex; and (2) detecting, as described herein, the quantity of binding complex in the sample. Detection of little to no binding complex is indicative of homozygous deletion of the MTAP gene complex.

In still another embodiment, the invention is directed to methods of treating a cancer patient with a therapeutically effective dose of a therapy regimen directed to an MTAP deficient cancer including the following steps: (1) providing an embedded biological sample from said patient; (2) contacting the embedded sample with a binding agent that specifically forms a binding complex with human MTAP protein in the embedded sample; (3) detecting the quantity of binding complex in the sample, whereby cancers with low or no detectable binding complex to human MTAP protein indicate MTAP deficient cancers amenable to treatment; and (4) administering a therapeutically effective amount of a therapy regimen directed to an MTAP deficient cancer. A preferred therapy regimen includes a drug that inhibits de novo purine synthesis. Preferred de novo purine synthesis inhibitors include L-alanosine, 10-propargyl-10-deazaminopterin (PDX), N-(4-(((2,4-diamino-6-pteridinyl)methyl) methylamino)benzoyl)-L-glutamic acid) (methotrexate), AG2037 (Agouron/Pfizer), 4-aminopteroylglutamic acid (aminopterin), 2,4-diamino-5-methyl-6-[[(3,4,5-trimethoxyphenyl)amino]methyl]quinazoline (trimetrexate), pyritrexim, 10-ethyl-deaza-aminopterin (edatrexate), 4'-methylene-10-deazaminopterin (MDAM), 10-propargyl-5,8-dideazafolic acid (PDDF), N-[5-[N-(3,4-dihydro-2-methyl-4-oxoquinazolin-6-ylmethyl)-N-methylamino]-2-thenoyl-L-glutamic acid (raltitrexed; ZD 1694, Tomudex), N-[4-[2-(2-amino-3,4-dihydro-4-oxo-7H-pyrrolo[2,3-d]-pyrimidin-5-yl)ethyl]-benzoyl]-L-glutamic acid (LY231514; Lilly), 6-(2'-formyl-2'naphthyl-ethyl)-2-amino-4(3H)-oxoquinazoline (LL95509), (6R,S)-5,10-dideazatetrahydrofolic acid (DDATHF), 4-[2-(2-amino-4-oxo-4,6,7,8-tetrahydro-3Hpyrimidino[5,4,6] [1,4]-thiazin-6yl)-(S)-ethyl]-2,5-thienoylamino-L-glutamic acid (AG2034), and N-[5-(2-[(2,6-diamino-4(3H)-oxopyrimidin-5-yl)thio]ethyl)thieno-2-yl]-L-glutamic acid (AG2009), 6R2',5'thienyl5,10-dideazatetrahydrofolic acid (LY309887), (S)-2-[4-[N-[(3,4-dihydro-2,7-dimethyl-4-oxo-6-quinazolinyl)methyl]-N-prop-2-ynylamino]-2-fluorob enzamido]-4-(1H-1,2,3,4-tetrazol-5-yl)butyric acid (ZD9331), N-[4-[N-[(3,4-dihydro-2,7-dimethyl-4-oxo-6-quinazolinyl)methyl]-N-prop-2- ynylamino]-2-fluorobenzoyl]-L-glutamic acid (ZM214888), N(alpha)-[4-[5-(2,4-diaminoteridin-6-yl)pent-1-yn-4-yl]benzoyl]-N(delta)-hemiphthaloyl-L-ornithine, or N(alpha)-(4-amino-4-deoxypteroyl)-N(delta)-hemiphthaloyl-L-ornithine (PT523). Preferred cancers for treatment include non-Hodgkin's lymphomas, mesotheliomas, glioblastomas, gliomas, non-small cell lung cancers, leukemias, bladder cancers, pancreatic cancers, soft tissue sarcomas, astrocytomas, osteosarcomas, head and neck cancers, or myxoid chondrosarcomas.

BRIEF DESCRIPTION OF THE DRAWINGS

This patent application file contains at least one drawing executed in color. Copies of this patent application publication with color drawing(s) will be provided by the U.S. Patent and Trademark Office upon request and payment of the necessary fee

FIG. 2 depicts an immunohistochemistry blot of paraffin-embedded glioblastoma multiforme using anti-MTAP monoclonal antibody produced by hybridoma cell line PTA-5001.

DETAILED DESCRIPTION OF THE INVENTION

Figure 1:
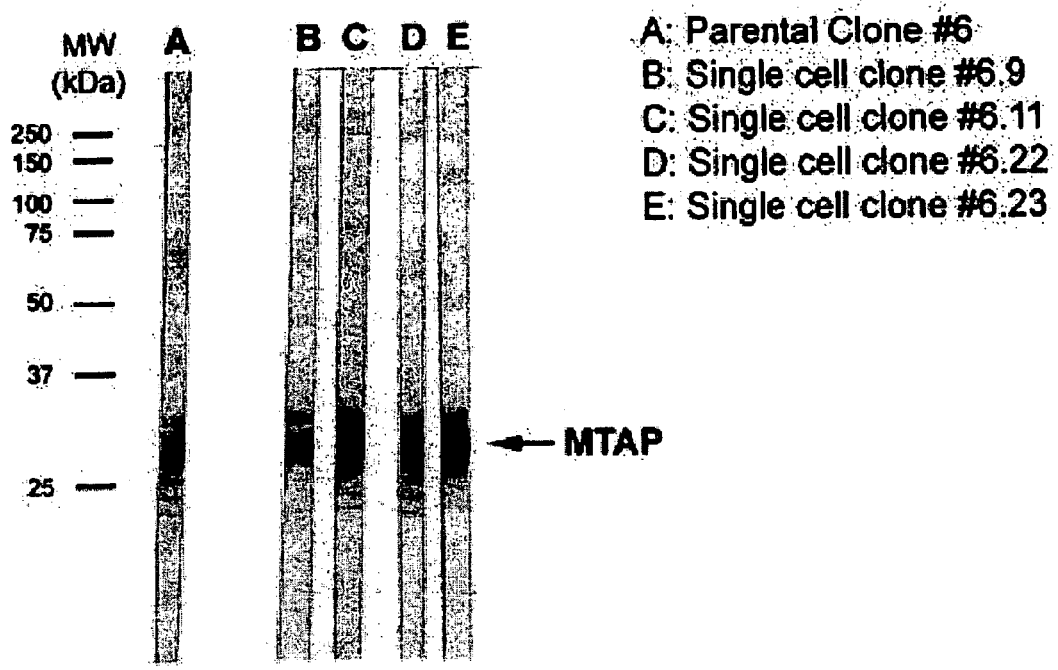
FIG. 1 depicts a Western blot of human MTAP protein using the antibodies produced by four subclones of hybridoma clone 6.

As used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

I. Definitions

The terms "MTAP-binding composition" or "MTAP-binding agent" refer to molecules that bind with specificity to human MTAP protein or a fragment thereof. The molecule may be a polymer, chemical reagent, an antibody, as defined herein, and other MTAP-binding proteins.

The terms "binding agent:MTAP protein complex," and "binding complex" as used herein, refer to a complex of an MTAP-binding agent and human MTAP protein. Specific binding of the binding agent means that the binding agent has a specific binding site that recognizes a site on the human MTAP protein. For example, antibodies raised to the human MTAP protein and recognizing an epitope on the human MTAP protein are capable of forming a binding agent:MTAP protein complex by specific binding. Typically, the formation of a binding agent:MTAP protein complex allows the detection of MTAP protein in a mixture of other proteins and biologics.

The term "antibody:MTAP protein complex" refers to an MTAP-binding agent:MTAP protein complex in which the MTAP-binding agent is an antibody. The antibody may be monoclonal, polyclonal or even an antigen binding fragment of an antibody.

The terms "antigenic determinant", or "epitope" as used herein, refer to the specific portion of an antigen to which an antibody binds.

An "immunogenic epitope", as used herein, is defined as a portion of a protein that elicits an antibody response in an animal, as determined by any method known in the art, for example, by the methods for generating antibodies (See, for example, Geysen et al. (1983) Proc. Natl. Acad. Sci. USA 81:3998–4002).

The terms "specific binding" or "specifically binding", as used herein, in reference to the interaction of an MTAP-binding agent, such as an antibody, a protein, or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the specificity can be demonstrated by a competition assay using labeled and unlabeled epitope A. Unlabeled epitope A will reduce the amount of labeled epitope A bound to the antibody. Antibodies specific for a particular human MTAP epitope may recognize proteins highly similar to the MTAP protein.

The phrase "specifically binds to an antibody" or "specifically immunoreactive with", when referring to a protein or peptide, refers to a binding reaction which is determinative of the presence of the protein in the presence of a heterogeneous population of proteins and other biological components. Thus, under designated immunoassay conditions, the specified binding agents, e.g., antibodies bind to a particular protein and do not significantly bind other proteins present in the sample. Specific binding to an antibody under such conditions may require an antibody that is selected for its specificity for a particular protein. For example, antibodies raised to the human MTAP protein immunogen with the amino acid sequence depicted in SEQ ID NO: 1 can be selected to obtain antibodies specifically immunoreactive with that MTAP protein and not with other proteins. These antibodies could recognize proteins highly similar to the human MTAP protein.

As used herein, the term "antibody" refers to intact molecules as well as fragments thereof, such as Fab, F(ab')$_2$, and Fv, which are capable of binding the antigenic determinant. Thus, use of the term "antibody" in this specification is understood to include whole antibodies and useful fragments of antibodies. Antibodies that bind human MTAP protein can be prepared using intact polypeptides or fragments containing small peptides of interest as the immunizing antigen. The polypeptide or peptide used to immunize an animal can be derived from the translation of RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

As used herein, the term "human MTAP protein," when used in a protein context, means a protein having the amino acid sequence as shown in SEQ ID NO: 1 or a fragment of such a protein that can be used in an aspect of the present invention, e.g., used to raise antibody specific for human MTAP protein, used as a positive control to confirm binding of an MTAP-binding agent to human MTAP protein, and other uses. Thus, use of the term "human MTAP protein" or "MTAP protein" in this specification is understood to include full-length MTAP protein, including trimeric and dimeric forms, and useful fragments of human MTAP protein. A human MTAP protein may also be derivatized. A human MTAP protein can interact with an MTAP-binding agent (as defined herein). These MTAP-binding agents, e.g., antibodies, typically bind to the MTAP protein with high affinity, e.g., at least about 100 nM, usually better than about 30 nM, preferably better than about 10 nM, and more preferably at better than about 3 nM.

The term "polypeptide" as used herein includes a fragment or segment of human MTAP protein, and includes a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. A polypeptide of human MTAP can include all the amino acids represented in SEQ ID NO: 1.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes); each monoclonal antibody is directed against a single determinant on the antigen.

The term "biological sample" is used herein in its broadest sense. A biological sample suspected of containing human MTAP protein or a gene encoding for human MTAP protein may comprise one or more cells, an extract from cells, blood, tissue, and the like.

The term "fixed", as used herein means treatment of a biological sample which results in preservation of histological detail. Such treatment can stabilize the proteins in the specimen, prevent changes to the sample caused by such things as mold, bacteria, and/or stops the continuation of enzyme metabolic processes (autolysis). Fixation can also change soluble substances within the cell to insoluble substances and protect the specimen from the denaturing effects of dehydrating agents and subsequent processing steps.

The term "MTAP gene complex" is the p14-p16-MTAP gene segment. This region comprises about a 200 kb region on chromosome 9p21-22.

As used herein, an "immunoassay" is an assay that utilizes an antibody to specifically bind to the analyte (e.g., human MTAP protein). The immunoassay is thus characterized by detection of specific binding of human MTAP protein or a fragment thereof to an antibody, i.e., detection of an antibody:MTAP protein complex. Thus, an immunoassay detects human MTAP protein using an antibody as an MTAP-binding agent, as opposed to the use of other physical or chemical properties to isolate, target, and quantify the analyte.

The term "immunohistochemistry" means a technique used to detect the presence of an antigen in histological samples.

The term "effusion" as used herein means an abnormal collection of fluid in a body cavity.

The phrase "detecting the quantity of", as used herein, includes detection methods that result in an objective quantification of the entity to be detected (e.g., human MTAP protein or MTAP-binding complex), as well as subjective quantifications (e.g., intensity of staining). Examples of objective quantifications include detecting the gram or milligram quantity of the entity. Examples of subjective quantifications include detecting the presence or absence of an entity, or the relative presence or absence of an entity. Such subjective quantifications may include the use of a scale, e.g., 0 to 4 pluses, with 0 indicating absence of the entity and 4+indicating detection of a large quantity of the entity.

The terms "nucleic acid molecule" and "polynucleotide" are used interchangeably in this application. These terms refer to any polyribonucleotide or polydeoxribonucleotide, which may be unmodified RNA or DNA or modified RNA or DNA. These terms are intended to include DNA molecules (e.g., cDNA) and RNA molecules (e.g., mRNA) and analogs of the DNA or RNA generated using nucleotide analogs.

A kit is any manufacture (e.g. a package or container) comprising at least one reagent, e.g., an MTAP-binding agent, for specifically detecting human MTAP. The manufacture is preferably promoted, distributed, or sold as a unit for performing the methods of the present invention.

The terms "therapeutically effective amount" and "therapeutically effective dosage" as used herein refer to that amount of the compound being administered which will relieve to some extent one or more of the symptoms of the disorder being treated. In reference to the treatment of cancer, a therapeutically effective amount refers to that amount which has the effect of (1) reducing the size of the tumor; (2) inhibiting (that is, slowing to some extent, preferably stopping) tumor metastasis; (3) inhibiting to some extent (that is, slowing to some extent, preferably stopping) tumor growth; and/or, (4) relieving to some extent (or, preferably, eliminating) one or more symptoms associated with the cancer.

As used herein the term "therapy regimen directed to an MTAP deficient cancer" means the use of a drug, combinations of drugs, or combinations of drugs and other cancer therapeutic measures, such as radiation therapy, which have been designed to take advantage of cancer cells having no or little MTAP protein.

II. Nucleic Acids

Techniques for nucleic acid manipulation of genes encoding MTAP proteins, e.g., subcloning nucleic acid sequences encoding polypeptides into expression vectors, labeling probes, DNA hybridization, and the like are described generally in, e.g., Sambrook et al., Molecular Cloning: A Laboratory Manual, 3$^{rd}$ ed. (2001) Cold Spring Harbor Press, Cold Spring Harbor, N.Y.; Glover, ed., DNA Cloning: A Practical Approach, Volumes I and II, 2nd (1995), both of which are incorporated herein by reference. See also, Coligan, et al. (1987 and periodic supplements) Current Protocols in Molecular Biology Greene/Wiley, New York, N.Y.; also incorporated herein by reference.

There are various methods of isolating the DNA sequences encoding MTAP proteins. See, e.g., Norbori et al. (1996), Proc. Natl. Acad. Sci. USA 93:6203–6208; Ragione et al. (1996) Biochem. Biophys. Res. Comm. 223:514–519; Olopade et al. (1995) Proc. Natl. Acad. Sci. USA 92:6489–6493; all incorporated herein by reference. For example, DNA can be isolated from a genomic or cDNA library using labeled oligonucleotide probes having sequences identical or complementary to the sequences disclosed herein. Full-length probes may be used, or oligonucleotide probes may be generated by comparison of the sequences disclosed with other proteins and selecting specific primers. Such probes can be used directly in hybridization assays to isolate DNA encoding MTAP proteins, or probes can be designed for use in amplification techniques such as PCR, for the isolation of DNA encoding MTAP proteins.

To prepare a cDNA library, mRNA is isolated from cells that express the MTAP protein. cDNA is prepared from the mRNA and ligated into a recombinant vector. The vector is transfected into a recombinant host for propagation, screening and cloning. Methods for making and screening cDNA libraries are well known. See Gubler et al. (1983) *Gene* 25:263–269; Sambrook et al., supra; or Coligan et al., supra.

For a genomic library, the DNA can be extracted from tissue and either mechanically sheared or enzymatically digested to yield fragments of about 12–20 kb. The fragments are then separated by gradient centrifugation and cloned in bacteriophage lambda vectors. These vectors and phage are packaged in vitro, as described, e.g., in Sambrook et al., supra or Coligan et al., supra. Recombinant phage are analyzed by plaque hybridization as described in Benton et al. (1977) *Science* 196:180–182. Colony hybridization is carried out as generally described in, e.g., Grunstein et al. (1975) *Proc. Natl. Acad. Sci. USA* 72:3961–3965.

DNA encoding an MTAP protein can be identified in either cDNA or genomic libraries by its ability to hybridize with the nucleic acid probes described herein, for example in colony or plaque hybridization experiments. The corresponding DNA regions are isolated by standard methods familiar to those of skill in the art. See Sambrook et al., supra.

Various methods of amplifying target sequences, such as the polymerase chain reaction, can also be used to prepare DNA encoding MTAP proteins. Polymerase chain reaction (PCR) technology is used to amplify such nucleic acid sequences directly from mRNA, from cDNA, and from genomic libraries or cDNA libraries. The isolated sequences encoding MTAP proteins may also be used as templates for PCR amplification.

In PCR techniques, oligonucleotide primers complementary to two 5' regions in the DNA region to be amplified are synthesized. The polymerase chain reaction is then carried out using the two primers. See Innis et al. (eds.) (1990) *PCR Protocols: A Guide to Methods and Applications* Academic Press, San Diego, Calif. Primers can be selected to amplify the entire regions encoding a selected full-length MTAP protein or to amplify smaller DNA segments as desired. Once such regions are PCR-amplified, they can be sequenced and oligonucleotide probes can be prepared from sequence obtained using standard techniques. The nucleotide sequence for the cDNA of human MTAP has been deposited with GenBank under accession number U22233 (SEQ ID NO:2).

Oligonucleotides for use as probes can be chemically synthesized according to the solid phase phosphoramidite triester method first described by Beaucage et al. (1983) *Tetrahedron Lett.* 22(20): 1859–1862, or using an automated synthesizer, as described in Needham-VanDevanter et al. (1984) *Nucleic Acids Res.* 12:6159–6168. Purification of oligonucleotides can be performed e.g., by native acrylamide gel electrophoresis or by anion-exchange HPLC as described in Pearson et al. (1983) *J. Chrom.* 255:137–149. The sequence of the synthetic oligonucleotide can be verified using the chemical degradation method of Maxam and Gilbert in Grossman and Moldave (eds.) (1980) *Methods in Enzymology* 65:499–560 Academic Press, New York.

III. Proteins

A. Producing Human MTAP Polypeptide or Polypeptide Fragments

DNAs, which encode human MTAP protein or fragments thereof, can be obtained by chemical synthesis, screening cDNA libraries, or by screening genomic libraries prepared from a wide variety of cell lines or tissue samples.

These DNAs can be expressed in a wide variety of host cells for the synthesis of a full-length protein or fragments that can, e.g., be used to generate polyclonal or monoclonal antibodies; for binding studies; for construction and expression of modified molecules; and for structure/function studies. Each of these human MTAP polypeptides can be expressed in host cells that are transformed or transfected with appropriate expression vectors. The polypeptides may be expressed as fusions with other proteins.

Expression vectors are typically self-replicating DNA or RNA constructs containing the desired MTAP gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome-binding site, and sequences that terminate transcription and translation. Expression vectors also usually contain an origin of replication that allows the vector to replicate independently from the host cell.

The vectors described herein contain DNAs, which encode human MTAP protein or a fragment thereof, typically encoding, e.g., a biologically active polypeptide or protein. The DNA can be under the control of a viral promoter and can encode a selection marker. This invention includes the use of such expression vectors which are capable of expressing eukaryotic cDNA coding for human MTAP in a prokaryotic or eukaryotic host, where the vector is compatible with the host and where the eukaryotic cDNA coding for the protein is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the protein or its fragments in various hosts using vectors that do not contain a replication origin that is recognized by the host cell. It is also possible to use vectors that cause integration of an MTAP gene or its fragments into the host DNA by recombination, or to integrate a promoter that controls expression of an endogenous gene.

Vectors, as used herein, comprise plasmids, viruses, bacteriophage, integratable DNA fragments, and other vehicles that enable the integration of DNA fragments into the genome of the host. Expression vectors are specialized vectors that contain genetic control elements that effect expression of operably linked genes. Plasmids are the most commonly used form of vector but all other forms of vectors that serve an equivalent function are suitable for use herein. See, e.g., Pouwels et al. (1985 and Supplements) *Cloning Vectors: A Laboratory Manual* Elsevier, N.Y.; and Rodriquez et al. (eds.) (1988) *Vectors: A Survey of Molecular Cloning Vectors and Their Uses* Buttersworth, Boston, Mass.

Suitable host cells include prokaryotes, lower eukaryotes, and higher eukaryotes. Prokaryotes include both gram-negative and gram-positive organisms, e.g., *E. coli* and *B. subtilis*. Lower eukaryotes include yeasts, e.g., *S. cerevisiae*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or its derivatives. Vectors that can be used to express human MTAP proteins or fragments include, but are not limited to, such vectors as those containing the lac promoter (pUC-series); trp promoter (pBR322-trp); Ipp promoter (the pIN-series); lambda-pp or pR promoters (pOTS); or hybrid promoters such as ptac (pDR540). See Brosius, et al. (1988) "*Expression Vectors Employing Lambda-, trp-, lac-, and Ipp-derived Promoters*", in Rodriguez et al.(eds.) Vectors: *A Survey of Molecular Cloning Vectors and Their Uses* 10:205–236 Buttersworth, Boston, Mass.

Lower eukaryotes, e.g., yeasts and Dictyostelium, may be transformed with an MTAP gene sequence containing vectors. Yeast vectors typically consist of a replication origin (unless of the integrating type), a selection gene, a promoter, DNA encoding the desired protein or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic tissue culture cells may be used as host cells for expression of human MTAP protein. In principle, most any higher eukaryotic tissue culture cell line may be used, e.g., insect baculovirus expression systems, whether from an invertebrate or vertebrate source. However, mammalian cells are preferred to achieve proper processing, both cotranslationally and posttranslationally. Transformation or transfection and propagation of such cells are routine in the art. Useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (e.g., if genomic DNA is used), a polyadenylation site, and a transcription termination site. These vectors also may contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pcDNA1; pCD, see Okayama et al. (1985) *Mol. Cell Biol.* 5:1136–1142; pMC1neo Poly-A, see Thomas et al. (1987) *Cell* 51:503–512; and a baculovirus vector such as pAC 373 or pAC 610.

In certain instances, the MTAP polypeptides or fragments thereof need not be glycosylated to elicit biological responses in certain assays. However, it may be desirable to express a human MTAP polypeptide in a system which provides a specific or defined glycosylation pattern. In this case, the usual pattern will be that provided naturally by the expression system. However, the pattern will be modifiable by exposing the polypeptide, e.g., in unglycosylated form, to appropriate glycosylating proteins introduced into a heterologous expression system. For example, a human MTAP gene may be co-transformed with one or more genes encoding mammalian or other glycosylating enzymes.

Conventional processes for synthesizing peptides can be used to prepare human MTAP protein, fragments, or derivatives. These include processes such as are described in Stewart et al. (1984) *Solid Phase Peptide Synthesis* Pierce Chemical Co., Rockford, Ill.; Bodanszky et al. (1984) *The Practice of Peptide Synthesis* Springer-Verlag, New York, N.Y.; and Bodanszky (1984) *The Principles of Peptide Synthesis* Springer-Verlag, New York, N.Y. See also Merrifield (1986) *Science* 232:341–347; and Dawson, et al. (1994) *Science* 266:776–779. For example, an azide process, an acid chloride process, an acid anhydride process, a mixed anhydride process, an active ester process (for example, p-nitrophenyl ester, N-hydroxysuccinimide ester, or cyanomethyl ester), a carbodiimidazole process, an oxidative-reductive process, or a dicyclohexylcarbodiimide (DCCD)/ additive process can be used. Solid phase and solution phase syntheses are both applicable to the foregoing processes.

The prepared protein and fragments thereof can be isolated and purified from the reaction mixture by means of peptide separation, for example, by extraction, precipitation, electrophoresis and various forms of chromatography, and the like. Purification can be accomplished by use of known protein purification techniques or by the use of the antibodies or binding partners herein described, e.g., in immunoabsorbant affinity chromatography. Immunoabsorbant affinity chromatography is carried out by first linking the antibodies to a solid support and contacting the linked antibodies with solubilized lysates of appropriate source cells, lysates of other cells expressing the protein, or lysates or supernatants of cells producing the proteins as a result of DNA techniques, see below.

Multiple cell lines may be screened for one which expresses the appropriate protein at a decreased or high level compared with other cells. Human MTAP protein can be isolated from natural sources, or by expression from a transformed cell using an appropriate expression vector. Purification of the expressed protein is achieved by standard procedures, or may be combined with engineered means for effective purification at high efficiency from cell lysates or supernatants. FLAG or 6×His tag segments can be used for such purification features.

The human MTAP protein amino acid sequence is provided in SEQ ID NO: 1. The sequence allows preparation of peptides to generate antibodies to recognize such segments. Moreover, affinity reagents allow detection and purification of more protein, including full-length or recombinant forms.

An isolated MTAP gene DNA can be readily modified by nucleotide substitutions, nucleotide deletions, nucleotide insertions, and inversions of nucleotide stretches. These modifications result in novel DNA sequences which encode MTAP proteins, or fragments thereof having highly similar physiological, immunogenic, or antigenic activity as wild-type MTAP protein. Modified sequences can be used to produce mutant antigens or to enhance expression. Enhanced expression may involve gene amplification, increased transcription, increased translation, and other mechanisms. Such mutant MTAP protein derivatives include predetermined or site-specific mutations of the respective protein or its fragments.

"Mutant MTAP protein" encompasses a polypeptide having an amino acid sequence which differs from that of the human MTAP protein as found in nature, whether by way of deletion, substitution, or insertion. Generally, the variant will share many physicochemical and biological activities, e.g., antigenic or immunogenic, with wild-type human MTAP, and contain most or all of the disclosed sequence.

The present invention also includes recombinant proteins, e.g., heterologous fusion proteins using segments from these proteins. A heterologous fusion protein is a fusion of proteins or segments that are naturally not normally fused in the same manner. Thus, the fusion product of an immunoglobulin with a respective MTAP polypeptide is a continuous protein molecule having sequences fused in a typical peptide linkage, typically made as a single translation product and exhibiting properties derived from each source peptide. A similar concept applies to heterologous nucleic acid sequences.

"Derivatives" of these MTAP antigens include amino acid sequence mutants, glycosylation variants, and covalent or aggregate conjugates with other chemical moieties. Covalent derivatives can be prepared by linkage of functionalities to groups which are found in the MTAP protein amino acid side chains or at the N- or C-termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species. Covalent attachment to carrier proteins may be important when immunogenic moieties are haptens.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents. Also, proteins comprising substitutions are encompassed, which should retain substantial immunogenicity, to produce antibodies which recognize a protein of SEQ ID NO: 1. Alternatively, proteins which begin and end at structural domains will usually retain antigenicity and cross immunogenicity.

A major group of derivatives are covalent conjugates of the MTAP proteins or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Other derivatives of human MTAP may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a human MTAP protein antigen can be immobilized by covalent bonding to a solid support such as cyanogen bromide-activated Sepharose, by methods which are well known in the art, or adsorbed onto polyolefin surfaces, with or without glutaraldehyde cross-linking, for use in an assay or purification of anti-MTAP protein antibodies. The MTAP protein or fragments thereof can also be labeled with a detectable group, e.g., radioiodinated by the chloramine T procedure, covalently bound to rare earth chelates, or conjugated to another fluorescent moiety for use in diagnostic assays. Purification of human MTAP or fragments thereof may be effected by immobilized antibodies.

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between human MTAP and its specific antibody. A two-site, monoclonal-based immunoassay utilizing monoclonal antibodies reactive to two non-interfering human MTAP epitopes is preferred, but a competitive binding assay may also be employed (Maddox (1983) *J. Exp. Med.* 158:1211–1216).

Fragments which function as epitopes may be produced by any conventional means. (See, e.g., Houghten (1985) *Proc. Natl. Acad. Sci. USA* 82:5131–5135, further described in U.S. Pat. No. 4,631,211).

In the present invention, antigenic epitopes preferably contain a sequence of at least 4 to 7, more preferably at least 8 to 40, and, most preferably, between about 15 to about 30 amino acids. Preferred polypeptides comprising immunogenic or antigenic epitopes of human MTAP are at least 4, 10, 15, 20, 25, 30, 35, 40, 45, 50, 55, 60, 65, 70, 75, 80, 85, 90, 95, or 100 amino acid residues in length up to and including the complete amino acid sequence of the protein. Methods for obtaining these polypeptides are described herein. Many conventional techniques in protein biochemistry and immunology are used. Such techniques are well known and are explained in Mayer et al. (1987) *Immunochemical Methods in Cell and Molecular Biology* Academic Press, London; Scopes (1987) *Protein Purification: Principles and Practice*, $2^{nd}$ ed. (Springer-Verlag, N.Y.), Weir et al. (1986) *Handbook of Experimental Immunology* $4^{th}$ ed. Blackwell Scientific Publications, and Deutscher (ed.) (1990) *Guide to Protein Purification, Meth. Enzymol.* 182: 529–539 Acad. Press, San Diego.

Non-limiting examples of antigenic polypeptides or peptides that can be used to generate MTAP-specific antibodies include: a polypeptide comprising, or alternatively consisting of, human MTAP amino acid residues (see, SEQ ID NO: 1) from about amino acid residues 18–28, 75–85, 93–103, 143–150, 170–180, or 220–245. In this context, "about" means the particularly recited ranges and ranges larger or smaller by several, a few, 10, 5, 4, 3, 2 or 1 amino acid residues at either or both the amino- and carboxy-termini. These polypeptide fragments have been determined to bear antigenic epitopes of human MTAP polypeptide by the antigenicity analysis of Hopp et al. ((1981) *Proc. Natl. Acad. Sci. USA* 86:152–156).

Additional non-exclusive preferred antigenic epitopes include the antigenic epitopes disclosed herein, as well as portions thereof. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al. (1984) *Cell* 37:767–778; Sutcliffe et al. (1983) *Science* 219:660–666); Bittle et al. (1985) *J. Gen. Virol.* 66:2347–2354).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., supra. If in vivo immunization is used, animals may be immunized with free peptide; however, anti-peptide antibody titer may be boosted by coupling the peptide to a macromolecular carrier, such as keyhole limpet hemacyanin (KLH), albumin or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. If the polypeptide is of sufficient length (at least about, 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody that can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

The human MTAP polypeptide or fragments thereof comprising an immunogenic or antigenic epitope can be fused to other polypeptide sequences. For example, MTAP polypeptides or fragments thereof may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al. (1988) *Nature*, 331:84–86. Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al. (1995) *J. Biochem.*, 270: 3958–3964.

Nucleic acids encoding the above epitopes can also be recombined with a gene of interest as an epitope tag (e.g., the hemagglutinin ("HA") tag, 6×His tag or flag tag) to aid in detection and purification of the expressed polypeptide. For example, Janknecht et al. ((1991), *Proc. Natl. Acad. Sci. USA* 88:8972–8976) described a system that allows for the ready purification of non-denatured fusion proteins expressed in human cell lines. In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

IV. Antibodies

As discussed herein, antibodies (polyclonal or monoclonal) can be raised to human MTAP protein, including individual, polymorphic, allelic, strain, or species variants, and fragments thereof, both in their naturally occurring (full-length) forms and in their recombinant forms. Anti-idiotypic antibodies may also be used.

Antibody fragments, which contain specific binding sites for human MTAP, may also be generated. For example, such fragments include, without limitation, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) *Science* 254:1275–1281).

Antibodies, including antigen binding fragments, specific for human MTAP or its fragments are useful in diagnostic applications to detect the presence or absence of human MTAP and/or its fragments. Such diagnostic assays can employ lysates, live cells, fixed cells, cell cultures, cell extracts, body fluids, and further can involve the detection of antigens in serum, or the like. Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. For example, as described herein, unlabeled antibodies can be employed by using a second antibody which is labeled and which recognizes the antibody to the human MTAP protein or to a particular fragment thereof. See, e.g., Harlow and Lane (1988) *Antibodies: A Laboratory Manual*, supra; Chan (ed.) (1987) *Immunoassay: A Practical Guide*, supra Academic Press, Orlando, Fl; Price and Newman (eds.) (1991) *Principles and Practice of Immunoassay* Stockton Press, NY; and Ngo (ed.) (1988) *Nonisotopic Immunoassay* Plenum Press, NY. In particular, the reagents may be useful for determining the presence or absence of MTAP in biological samples. The assay may be directed to histological analysis of a biopsy, or evaluation of MTAP in a blood or tissue sample.

A. Antibody Production

As discussed herein, a number of immunogens may be used to produce antibodies specifically reactive with human MTAP. Recombinant protein is the preferred immunogen for the production of monoclonal or polyclonal antibodies.

Naturally occurring protein may also be used either in pure or impure form. Synthetic peptides made using the human MTAP protein sequence described herein may also used as an immunogen for the production of antibodies to the human MTAP protein. Recombinant protein can be expressed in eukaryotic or prokaryotic cells as described herein, and purified as described. The product is then injected into an animal capable of producing antibodies. Either monoclonal or polyclonal antibodies may be generated for subsequent use in immunoassays to measure the protein.

Methods of producing polyclonal antibodies are known to those of skill in the art. In brief, an immunogen, preferably a purified protein, is mixed with an adjuvant and animals are immunized with the mixture. The animal's immune response to the immunogen preparation is monitored by taking test bleeds and determining the titer of reactivity to the protein of interest, for example, using an ELISA assay. When appropriately high titers of antibody to the immunogen are obtained, blood is collected from the animal and antisera are prepared. Further fractionation of the antisera to enrich for antibodies reactive to the protein can be done if desired. See, e.g., Harlow et al. (1988) *Antibodies: A Laboratory Manual* CSH Press.

Monoclonal antibodies may be obtained by various techniques familiar to those skilled in the art. Briefly, spleen cells from an animal immunized with a desired antigen are immortalized, commonly by fusion with a myeloma cell. See, e.g., Kohler and Milstein (1976) *Eur. J. Immunol.* 6:511–519, which is incorporated herein by reference. Alternative methods of immortalization include transformation with Epstein Barr Virus, oncogenes, or retroviruses, or other methods known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al. supra.

Antibodies, including binding fragments and single chain versions, against predetermined fragments of human MTAP can be raised by immunization of animals with conjugates of the fragments with carrier proteins as described above. Monoclonal antibodies are prepared from cells secreting the desired antibody. These antibodies can be screened for binding to normal or mutant MTAP proteins, or screened for agonistic or antagonistic activity. These monoclonal antibodies will usually bind with at least a $K_D$ of about less than $5\times10^4$ M, $5\times10^{-5}$ M, $10^{-5}$ M, $5\times10^{-6}$ M, $10^{-6}$ M, $5\times10^{-7}$ M, $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M. Methods for determining antibody binding affinities are reported in Heyningen (1986) *Methods in Enzymology* 121:472 and Qiu et al., (1996) *J. ofimmunol.*, 156:3350 (1996); all incorporated herein by reference.

Monoclonal antibodies may be prepared from various mammalian hosts, such as mice, rodents, primates, humans, etc. Description of techniques for preparing such monoclonal antibodies may be found in, e.g., Stites, et al. (eds.) Basic and Clinical Immunology (4th ed.) Lange Medical Publications, Los Altos, Calif., and references cited therein; Harlow (1986) *Monoclonal Antibodies: Principles and Practice* (2d ed.) Academic Press, New York, N.Y.; and particularly in Kohler and Milstein (1975) *Nature* 256: 495–497, which reports one method of generating monoclonal antibodies. Summarized briefly, this method involves injecting an animal with an immunogen to initiate a humoral immune response. The animal is then sacrificed and cells taken from its spleen, which are then fused with myeloma cells. The result is a hybrid cell or hybridoma that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Other suitable techniques involve selection of libraries of antibodies in phage or similar vectors. See, Huse et al. supra; and Ward et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance that provides for a detectable signal. A wide variety of labels and conjugation techniques are known and are reported extensively in both the scientific and patent literature. For instance, antibody molecules produced by a hybridoma can be labeled by metabolic incorporation of radioisotope-containing amino acids provided as a component in the culture medium. See, for example, Galfre et al. (1981) *Meth. Enzymol.* 73:3–46. The techniques of protein conjugation or coupling through activated functional groups are particularly applicable. See, for example, Avrameas et al. (1978) *Scand. J. Immunol., Vol.* 8, Suppl. 7:7–23; Rodwell et al. (1984) *Biotech.* 3:889–894, and U.S. Pat. No. 4,493, 795. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241.

The antibodies of this invention can also be used for affinity chromatography in isolating human MTAP protein. Columns can be prepared where the antibodies are linked to a solid support, e.g., particles, such as agarose, SEPHADEX, or the like, where a cell lysate may be passed through the column, the column washed, followed by increasing concentrations of a mild denaturant, whereby purified human MTAP protein will be released.

The antibodies may also be used to screen expression libraries for particular expression products. Usually the antibodies used in such a procedure will be labeled with a moiety allowing easy detection of presence of antigen by antibody binding.

Antibodies to human MTAP protein may be used for the analysis of, or identification of specific cell population components that express the respective protein. Further, antibodies to human MTAP may be used to screen biological samples, such as tumor specimens. Preferably, the biological samples are embedded and fixed, e.g., tumor biopsies embedded in paraffin and fixed with formalin. By assaying the expression products of cells that express or do not express human MTAP protein, it is possible to select patients that may benefit from treatments designed to take advantage of cancer cells that express low or no levels of MTAP protein. Further, since deletions of MTAP are often associated with deletions of other genes on chromosome 9, such as p16 and p14, the determination that a tumor cell does not express MTAP can be used as a surrogate marker for p16 and p14 deletions. Deletions of p16 and p14 in association with MTAP deletion are linked with advanced stage tumors.

In addition, the present invention includes antibodies that are capable of binding to the same antigenic determinant as the monoclonal antibody produced by hybridoma cell line ATCC PTA-5001, as described herein, or fragments thereof. Such antibodies would compete with the monoclonal antibodies produced by hybridoma cell line ATCC PTA-5001 for binding at that epitope. These include antibodies having the same antigenic specificity as the monoclonal derived from ATCC PTA-5001 but differing in species origin, isotype, binding affinity or biological functions (e.g., cytotoxicity). For example, class, isotype and other variants of the antibodies of the invention having the antigen-binding region of the antibody produced from hybridoma cell line PTA-5001 antibody can be constructed using recombinant class-switching and fusion techniques known in the art (see, e.g., Thammana et al. (1983) *Eur. J Immunol.* 13:614; Spira et al. (1984) *J. Immunol. Meth.* 74:307–15; Neuberger et al. (1984) *Nature* 312:604–608; and Oi et al. (1986) *Biotechniques*, 4(3):214–21). Thus, other chimeric antibodies or other recombinant antibodies (e.g., fusion proteins wherein the antibody is combined with a second protein such as a lymphokine or a tumor inhibitory growth factor) having the same binding specificity as the antibody produced from hybridoma cell line ATCC PTA-5001 antibody fall within the scope of this invention.

B. Immunoassays

A particular protein can be measured by a variety of immunoassay methods. For a review of immunological and immunoassay procedures in general, see Stites et al. (eds.) (1991) *Basic and Clinical Immunology* (7th ed.). Moreover, the immunoassays of the present invention can be performed in any of several configurations, which are reviewed extensively in Maggio (ed.) (1980) *Enzyme Immunoassay* CRC Press, Boca Raton, Fla.; Tijan (1985) "Practice and Theory of Enzyme Immunoassays," *Laboratory Techniques in Biochemistry and Molecular Biology*, Elsevier Science Publishers B. V., Amsterdam; and Harlow and Lane Antibodies, A Laboratory Manual, supra, each of which is incorporated herein by reference. See also Chan (ed.) (1987) *Immunoassay: A Practical Guide* Academic Press, Orlando, Fla.; Price et al. (eds.) (1997) *Principles and Practice of Immunoassay* ($2^{nd}$ ed), Groves Dictionaries, Inc.; Boenisch (ed.) (2001) *Handbook Immunochemical Staining Methods* DAKO Corp. Carpinteria, Calif., USA; and Ngo (ed.). (1988) *Non-isotopic Immunoassays* Plenum Press, NY; all incorporated herein by reference.

In general, immunoassay design considerations include preparation of antibodies (e.g., monoclonal or polyclonal) having sufficiently high-binding specificity for their antigen so the specifically bound antibody-antigen complex can be distinguished reliably from nonspecific interactions. The higher the antibody binding specificity, the lower the antigen concentration that can be detected. Currently preferred binding specificity is such that the binding protein has a binding affinity for the marker protein of greater than about $10^5$ $M^{-1}$ preferably greater than about $10^7$ $M^{-1}$.

Immunoassays for measurement of human MTAP protein can be performed by a variety of methods known to those skilled in the art. (see, e.g., U.S. Pat. Nos. 4,366,241; 4,376,110; 4,517,288; and 4,837,168). For a review of the general immunoassays, see also Asai (1993) *Methods in Cell Biology Volume 37: Antibodies in Cell Biology*, Academic Press, Inc. New York; Stites & Terr (1991) *Basic and Clinical Immunology* 7th Edition.

Immunological binding assays (or immunoassays) typically utilize a "capture agent" to specifically bind to and often immobilize the analyte (MTAP polypeptide). In preferred embodiments, the MTAP-binding agent is an antibody.

In brief, immunoassays to measure the protein can be competitive or noncompetitive. Noncompetitive immunoassays are assays in which the amount of captured analyte (in this case, MTAP) is directly measured. In a "sandwich" assay, for example, the binding agent (e.g., antibody) is bound directly or indirectly to a solid substrate where it is immobilized. These immobilized MTAP antibodies capture MTAP protein present in a biological sample (e.g., a blood sample). The MTAP protein thus immobilized is then bound by a labeling agent, such as a MTAP antibody bearing a label. Alternatively, the second antibody may lack a label, but it may, in turn, be bound by a labeled third antibody specific to antibodies of the species from which the second antibody is derived. Free labeled antibody is washed away and the remaining bound labeled antibody is detected (e.g., using a gamma detector where the label is radioactive).

In competitive assays, the amount of analyte (e.g., MTAP) present in the sample is measured indirectly by measuring the amount of an added (exogenous) analyte displaced (or competed away) from a capture agent (e.g., MTAP antibody) by the analyte present in the sample. In one competitive assay, a known amount of MTAP polypeptide is added to a sample with an unquantified amount of MTAP polypeptide, and the sample is contacted with a capture agent, e.g., an MTAP antibody that specifically binds MTAP. The amount of added MTAP polypeptide that binds to the MTAP antibody is inversely proportional to the concentration of MTAP present in the test sample.

Alternatively, a homogeneous immunoassay may be performed in which a separation step is not needed. In these immunoassays, the label on the protein is altered by the binding of the protein to its specific binding agent. This alteration in the labeled protein results in a decrease or increase in the signal emitted by label, so that measurement of the label at the end of the immunoassay allows for detection or quantitation of the protein.

Western blot analysis can be used to determine the presence or absence of human MTAP protein in a sample. Electrophoresis is carried out, e.g., on a tissue sample suspected of containing the protein. Following electrophoresis to separate the proteins, and transfer of the proteins to a suitable solid support such as a nitrocellulose filter, the solid support is incubated with an antibody reactive with the denatured protein. This antibody may be labeled, or alternatively may be it may be detected by subsequent incubation with a second labeled antibody that binds the primary antibody.

A preferred method, described herein, for determining the presence or absence of MTAP protein, in a biological sample, is immunohistochemistry (IHC). Immunohistochemistry allows for the evaluation of micro-anatomical detail and heterogeneity in tissues and tumors. Immunohistochemistry is advantageous over other methods of analyses because it is the only method that can directly localize proteins to individual cell types. Differences among gene expression of normal and tumor tissue can be detected while simultaneously noting the changes in cell number and composition. In contrast, techniques, such as Western blotting require the use of cell extracts; therefore, a possibility exists of contamination of different cell types.

For IHC, a primary MTAP-binding agent that recognizes human MTAP protein is introduced to a biological specimen.

The primary MTAP-binding agent can be, for example, selected from the group consisting of a chemical compound that specifically binds human MTAP, an antisera containing polyclonal antibodies specifically reactive with human MTAP protein, a monoclonal antibody that specifically binds with human MTAP protein, or antigen-binding fragments of monoclonal or polyclonal antibodies that specifically bind human MTAP protein. After incubation with the primary antibody, a wash can be performed to remove unbound antibody. Then, a secondary antibody, directed against the primary antibody and labeled with an enzyme, can be incubated with the biological specimen. During incubation, the secondary antibody will bind to the primary antibody. Alternatively, the second antibody may lack a label, but it may, in turn, be bound by a labeled third antibody specific to antibodies of the species from which the second antibody is derived.

In another embodiment, the primary MTAP-binding agent can be labeled with an enzyme thus eliminating the need for a second antibody. Alternatively, the labeled MTAP-binding agent can be labeled with biotin rather than an enzyme. Then, in an additional step, enzyme-labeled avidin or streptavidin is introduced to the sample and allowed to bind to the biotinylated antibody.

For immunohistochemistry, the tissue sample may be fresh or frozen or may be embedded, for example, in paraffin or other waxes, nitrocellulose, carbowax (also known as water soluble polyethylene glycol (see, Gao ed. (1993) "Polyethylene Glycol as an Embedment for Microscopy and Histochemistry," CRC Press, Inc. Boca Raton, Fl.), plastic, including resins such as acrylic and epoxy resins, or OCT embedded frozen blocks. Preferably, the samples are embedded in paraffin or other waxes, nictrocellulose, carbowax, or plastic. The samples can be fixed with a preservative, such as formalin, for example. A preferred embodiment of the invention is a formalin-fixed biological sample embedded in paraffin.

A preferred MTAP-binding agent for detecting the presence or absence of human MTAP protein in a biological sample is a monoclonal antibody the specifically binds to human MTAP protein.

Another preferred technique for determining the presence or absence of MTAP, using the antibodies described herein, is immunocytology. This technique is useful for the analysis of hematological cancers.

The MTAP-binding agents described herein are useful for determining the MTAP status of samples obtained from surgical biopsies, fine-needle biopsies, fine-needle aspiration biopsies, core-needle biopsies, effusions from body cavities, such as the abdominal cavity, the pleural cavities and the pericardial cavity, and cells collected from other bodily fluids, such as blood and urine and the like. Methods of obtaining such samples are known in the art. For example, an effusion sample can be collected by puncturing the chest wall or abdominal wall with a needle and evacuating the fluid. Samples from fine-needle aspirations, effusions or other bodily fluids can be spun onto slides using conventional centrifugation or a Cytospin® apparatus (Shandon, Runcorn, U.K.) or smeared onto an appropriate slide for staining and/or fixation. Cell blocks can also be prepared from such samples by concentrating the cells contained therein. For example, cells can be concentrated, e.g., by centrifugation. After concentration, the cells can be fixed in a suitable fixing agent, such as formalin or alcohol and then embedded into paraffin or other suitable material as done for tissue in surgical pathology. Concentrated cells can also be processed for ThinPrep preparation using, for example, a Cytyc ThinPrep® processor (Cytyc Corp Boxborough, Mass.).

Yet another preferred technique for determining the MTAP status of a cell, using the antibodies described herein, is Flow Cytometry (FACS). The theory of Flow Cytometry is discussed in Ormerod (ed) *Flow Cytometry: A Practical Approach* (IRL Press, Oxford. 1994); Shapiro, *Practical Flow Cytometry*. 3rd Edition; (Alan R Liss, Inc.). Givan, *Flow Cytometry. First Principles* (Wiley-Liss, New York, 1992.); Robinson (ed.) *Handbook of Flow Cytometry Methods*. (Wiley-Liss, New York, 1993)

1. Fixation

Fixation is an important step in immunohistochemical and immunocytochemical assays. Fixation stabilizes the proteins in the specimen and prevents changes caused by such things as mold, bacteria, and the continuation of enzyme metabolic processes (autolysis). Fixatives can also change soluble substances within the cell to insoluble substances. Fixatives also protect the specimen from the denaturing effects of dehydrating agents and subsequent processing steps.

Biological samples can be fixed using techniques known in the art. For example, air-drying can preserve blood smears. The smear can then be fixed using a fixative agent, such as, but not limited to, a high-grade methanol, anhydrous acetone, or formalin-based fixatives. Air-dried preparations may exhibit an overall lower MTAP antigen density, resulting in weak immunostaining. Thus, extended MTAP-binding agent incubation times may be needed.

Cytology smears may be fixed in 95% ethanol or spray-fixed with a carbowax containing alcoholic fluid. Samples prepared using a Cytospin apparatus can be fixed using fixative agents such as acetone, alcohol, formalin, or paraformaldehyde. Cryostat sections may be fixed using fixative agents such as alcohol or acetone.

Before embedding, biological samples may be fixed using, without limitation, formaldehyde-based fixatives, mercuric chloride-based fixatives, zinc-based fixatives, periodate-lysine-paraformaldehyde (PLP), glyoxal-based fixatives, Bouin's solution (contains formaldehyde, an aqueous saturated picric acid and glacial acetic acid), Hollande's Solution (contains cupric acetate that preserves red blood cell membranes, the granules of eosinophils and endocrine cells, and is capable of decalcifying small pieces of bone), ethanol, or acetone.

After fixation, specimens that contain bone may need to be decalcified. Most decalcifying agents contain acid. The acids used for decalcification may be either inorganic acids (hydrochloric and nitric) or organic acids (formic and acetic). Chelating agents may also be used for decalcifying. For example, ethylenediaminetetraacetic acid (EDTA) is a preferred chelating agent for decalcification.

2. Antigen Retrieval

Alternate terminologies for "antigen retrieval" include "epitope retrieval," "heat-induced epitope retrieval" (HIER), "target retrieval," and "target unmasking." Fixation may cause loss of immunoreactivity for many antigens. The immunoreactivity of fixed tissue antigens and samples in cell blocks can be improved using techniques known in the art. For example, proteolytic digestion with proteolytic enzymes, such as, but not limited to, trypsin, bromelain, chymotrypsin, ficin, pepsin, or pronase, prior to adding the MTAP-binding agent can improve immunoreactivity. Other suitable methods for epitope retrieval in embedded tissue sections and cell blocks include, heating, such as with, but not limited to, a microwave oven, autoclaves, steamers, water baths or pressure cookers. Another suitable method for restoring immunoreactivity includes combining enzymatic digestion with heating in the presence of a retrieval solution such as, but not limited to, citrate buffer (about pH 6.0), EDTA buffer of about pH 8.0, or 0.01 M TRIS-HCl of pH about 1 or about 10. Methods of antigen retrieval can also be used with some cytology specimens.

Antigen retrieval can be used for cytology slides, including Papanicolaou-stained slides. Heat induced antigen retrieval, if necessary, may be done using suitable methods, as described herein, such as water baths, pressure cookers, and microwave ovens and the like.

The immunoassay formats described above may employ labeled assay components, as described herein. The label can be in a variety of forms. The label may be coupled directly or indirectly to the desired component of the assay according to methods well known in the art. A wide variety of labels may be used. The component may be labeled by any one of several methods. Traditionally a radioactive label incorporating $^3H$, $^{125}I$, $^{35}S$, $^{14}C$, or $^{32}P$ is used. Non-radioactive labels include ligands that bind to labeled antibodies, fluorophores, chemiluminescent agents, enzymes, and antibodies that can serve as specific binding pair members for a labeled protein. The choice of label depends on, for example, the sensitivity required, ease of conjugation with the compound, stability requirements, and available instrumentation. For a review of various labeling or signal producing systems that may be used, see U.S. Pat. No. 4,391,904, which is incorporated herein by reference.

Antibodies reactive with a particular protein can also be measured by a variety of immunoassay methods, as discussed herein. For reviews of immunological and immunoassay procedures applicable to the measurement of antibodies by immunoassay techniques, see, e.g., Stites and Terr (eds.) *Basic and Clinical Immunology* (7th ed.) supra; Maggio (ed.) *Enzyme Immunoassay, supra*; and Harlow and Lane *Antibodies, A Laboratory Manual, supra*.

A variety of different immunoassay formats, separation techniques, and labels can also be used similar to those described above for the measurement of specific proteins. Moreover, many methods are known for evaluating selectivity of binding for specific protein or closely related proteins.

V. Results of Assays

Described herein are monoclonal antibodies, which specifically bind to human MTAP protein. These monoclonal antibodies can detect the absence or presence of MTAP protein in biological samples embedded, for example, in paraffin or other suitable material, such as other waxes, nitrocellulose, PEG, or plastic. In particular, the antibodies can detect human MTAP in formalin-fixed paraffin-embedded (FFPE) tissues. Using the assays described herein, the antibodies can detect MTAP in normal tissue while eliciting no positive staining in control cells, or tumor tissues that lack MTAP (see Table 1). The antibodies can also detect cells that produce low levels of MTAP as compared to normal cells. The antibodies also detect human MTAP in the nucleus of cells.

To develop an immunohistochemistry assay using the antibodies of the invention, a pretreatment analysis was performed on paraffin sections to determine a suitable antigen retrieval method. It was found that Heat-Induced Epitope Retrieval (H.I.E.R.) using a pressure cooker (BORG-BioCare Medical) at about 120° C. for about 3 minutes followed by trypsin for about one minute gave good results for the immunohistochemistry assays described herein. Also, a monoclonal antibody titer of about 20 µg/ml produced a suitable combination of staining intensity and low background staining and was the concentration used for the immunohistochemistry screening studies described herein.

For the assays described herein interpretation of stained slides was performed by microscopic examination. In general, a morphologic review of the tissue on the slide determined whether an adequate amount of tissue was present, and whether the designated tissue was appropriately represented. Samples failing to meet the above standards were rejected from the analysis and retested if adequate tissue remained. If adequate tissue was not available, the tissue was replaced by random sampling.

The scoring system included an analysis of staining intensity. The staining intensity of the test article was judged relative to the intensity of a control slide containing an adjacent section stained with a negative control antibody. Staining of the section labeled with the negative reagent control was considered "background." A "0" indicates no staining relative to background. A "1+" indicates weak staining. A "2+" indicates moderate staining, and a "3+" indicates strong staining. (see, Table 1) Using standard pathology practice, staining intensity was reported at the highest level of intensity observed in all tissue elements, except the distinctive tissue element where an expanded scoring scheme was reported.

Descriptive statistics were performed using Microsoft Excel. H-scores were calculated for the tumor and normal adjacent tissues according to the following formulas:

Long H-score=(3×% of cells staining 3+)+(2×% of cells staining 2+)+(1×% of cells staining 1+)

Short H-score (highest staining intensity observed×% of cells staining at that intensity).

In selecting a patient for treatment of an MTAP deficient cancer, a preferred long H score is about 50, more preferably about 20 and even more preferably about 5 or less.

Using these methods, forty-two fixed lung carcinoma specimens were tested using the anti-MTAP monoclonal antibody 6.9, which is produced from hybridoma cell line ATCC 5001. Out of 42 specimens, seven exhibited strong (3+) staining, 15 exhibited moderate (2+) staining, and ten exhibited weak (1+) staining. In ten lung carcinoma specimens, no staining of the neoplastic cells was observed (Table 1).

Seventeen specimens of pancreatic carcinoma were tested using anti-MTAP monoclonal antibody 6.9. Twelve specimens exhibited moderate to strong (2–3+) staining while five specimens exhibited no staining of neoplastic cells (Table 1).

Each of the eight sarcomas tested stained positively for the anti-MTAP monoclonal antibody. Staining intensities ranged from weak (1+) to strong (3+) staining. All five Leiomyosarcoma stained positively with the anti-MTAP monoclonal 6.9 with intensities ranging from weak (I+) to strong (3+). Two liposarcomas were tested and neither exhibited staining of the neoplastic cells. One extraskeletal osteosarcoma was tested with the anti-MTAP monoclonal antibody 6.9 and exhibited weak (1+) staining of the neoplastic cells. Two specimens of synovial sarcoma were tested; one exhibited moderate (2+) staining of neoplastic cells while the other exhibited weak (1+) staining of the neoplastic cells (Table 1).

In brain tumors, 46 tumor samples were analyzed with anti-MTAP monoclonal antibody 6.9, 4 exhibited strong (3+) staining, 5 exhibited moderate (2+) staining of neoplastic cells, 8 exhibited weak (1+) staining of the neoplastic cells, and 29 exhibited no staining of neoplastic cells.

Positive and negative controls tissues were included during each staining experiments. For MTAP-positive tissue controls, the MTAP-expressing cell line A427 (ATCC), 5 normal placental tissues and a tumor sample that was previously characterized as expressing MTAP were used. When possible, normal cells surrounding the tumor cells were also scored for MTAP positivity.

For MTAP-deleted tissue controls, the cell line A549 (homozygously deleted for MTAP) (ATCC) and a tumor block previously characterized as MTAP-deleted were used.

Neither monoclonal antibody 6.9 nor a chicken anti-MTAP polyclonal worked well in assays involving frozen tissues embedded in OCT.

In conclusion, the data obtained using the anti-MTAP monoclonal antibody are in accord with previously reported data obtained in the same tumor types using hybridization based techniques to detect the presence or absence of the MTAP gene at the DNA or RNA levels.

TABLE 1

| | Tissue Type | 3+ | Sub. | 2+ | Sub. | 1+ | Sub. | 0 | L | S |
|---|---|---|---|---|---|---|---|---|---|---|
| 1 | Extraskeletal Ostesarcoma | 0 | | 0 | | 20 | C,N | 80 | 20 | 20 |
| 2 | Glioma | 50 | C,N | 30 | C,N | 20 | C,N | 0 | 230 | 150 |
| 3 | Glioma | 0 | | 0 | | 0 | | 100 | 0 | 0 |
| 4 | Glioma | 0 | | 60 | C,N | 40 | C,N | 0 | 160 | 120 |
| 5 | Leiomyosarcoma | 5 | C | 45 | C | 40 | C | 10 | 145 | 15 |
| 6 | Leiomyosarcoma | 5 | C,N | 15 | C,N | 70 | C | 10 | 115 | 15 |
| 7 | Leiomyosarcoma | 0 | | 0 | | 10 | C | 90 | 10 | 10 |
| 8 | Leiomyosarcoma | 0 | | 10 | C | 70 | C | 20 | 90 | 20 |
| 9 | Leiomyosarcoma | 80 | C,N | 20 | C,N | 0 | | 0 | 280 | 240 |
| 10 | Liposarcoma | 0 | | 0 | | 0 | | 100 | 0 | 0 |
| 11 | Liposarcoma | 0 | | 0 | | 0 | | 100 | 0 | 0 |
| 12 | Non-Small Cell Lung CA | 0 | | 60 | C,N | 40 | C,N | 0 | 160 | 120 |
| 13 | Non-Small Cell Lung CA | 30 | N,C | 30 | N,C | 35 | C,N | 5 | 185 | 90 |
| 14 | Non-Small Cell Lung CA | 70 | N,C | 20 | N,C | 0 | | 5 | 250 | 210 |
| 15 | Non-Small Cell Lung CA | 80 | N,C | 10 | N,C | 0 | | 10 | 260 | 240 |
| 16 | Non-Small Cell Lung CA | 0 | | 0 | | 0 | | 100 | 0 | 0 |
| 17 | Non-Small Cell Lung CA | 0 | | 5 | N,C | 25 | C,N | 70 | 35 | 10 |
| 18 | Non-Small Cell Lung CA | 40 | N,C | 30 | N,C | 30 | C,N | 0 | 210 | 120 |
| 19 | Non-Small Cell Lung CA | 0 | | 60 | C,N | 40 | C,N | 0 | 160 | 120 |
| 20 | Non-Small Cell Lung CA | 0 | | 0 | | 0 | | 100 | 0 | 0 |
| 21 | Non-Small Cell Lung CA | 0 | | 0 | | 0 | | 100 | 0 | 0 |
| 22 | Non-Small Cell Lung CA | 0 | | 0 | | 0 | | 100 | 0 | 0 |
| 23 | Non-Small Cell Lung CA | 0 | | 40 | C,N | 60 | C,N | 0 | 140 | 80 |
| 24 | Non-Small Cell Lung CA | 0 | | 0 | | 0 | | 100 | 0 | 0 |
| 25 | Non-Small Cell Lung CA | 0 | | 0 | | 30 | C,N | 70 | 30 | 30 |
| 26 | Non-Small Cell Lung CA | 40 | C,N | 30 | C,N | 30 | C,N | 0 | 210 | 120 |
| 27 | Non-Small Cell Lung CA | 0 | | 60 | C,N | 30 | C,N | 10 | 150 | 120 |
| 28 | Non-Small Cell Lung CA | 0 | | 0 | | 0 | | 100 | 0 | 0 |
| 29 | Non-Small Cell Lung CA | 10 | C,N | 60 | C,N | 30 | C,N | 0 | 180 | 30 |
| 30 | Non-Small Cell Lung CA | 0 | | 60 | C,N | 40 | C,N | 0 | 160 | 120 |
| 31 | Non-Small Cell Lung CA | 0 | | 30 | C,N | 70 | C,N | 0 | 130 | 60 |
| 32 | Non-Small Cell Lung CA | 0 | | 0 | | 0 | | 100 | 0 | 0 |
| 33 | Non-Small Cell Lung CA | 40 | C,N | 40 | C,N | 20 | C,N | 0 | 220 | 120 |
| 34 | Non-Small Cell Lung CA | 0 | | 30 | C,N | 50 | C,N | 20 | 110 | 60 |
| 35 | Non-Small Cell Lung CA | 0 | | 0 | | 90 | C,N | 10 | 90 | 90 |
| 36 | Non-Small Cell Lung CA | 0 | | 0 | | 0 | | 100 | 0 | 0 |
| 37 | Non-Small Cell Lung CA | 0 | | 10 | C,N | 90 | C,N | 0 | 110 | 20 |
| 38 | Non-Small Cell Lung CA | 0 | | 0 | | 100 | C,N | 0 | 100 | 100 |
| 39 | Non-Small Cell Lung CA | 0 | | 60 | C,N | 40 | C,N | 0 | 160 | 120 |
| 40 | Non-Small Cell Lung CA | 0 | | 75 | C,N | 15 | C,N | 10 | 165 | 150 |
| 41 | Non-Small Cell Lung CA | 0 | | 0 | | 100 | C | 0 | 100 | 100 |
| 42 | Non-Small Cell Lung CA | 0 | | 40 | C,N | 50 | C,N | 10 | 130 | 80 |
| 43 | Non-Small Cell Lung CA | 0 | | 0 | | 0 | | 100 | 0 | 0 |
| 44 | Non-Small Cell Lung CA | 0 | | 0 | | 80 | C,N | 20 | 80 | 80 |
| 45 | Non-Small Cell Lung CA | 0 | | 0 | | 60 | C,N | 40 | 60 | 60 |
| 46 | Non-Small Cell Lung CA | 0 | | 0 | | 20 | N,C | 80 | 20 | 20 |
| 47 | Non-Small Cell Lung CA | 0 | | 0 | | 40 | C,N | 60 | 40 | 40 |
| 48 | Non-Small Cell Lung CA | 0 | | 10 | C,N | 70 | C,N | 20 | 90 | 20 |
| 49 | Non-Small Cell Lung CA | 0 | | 0 | | 10 | C,N | 90 | 10 | 10 |
| 50 | Non-Small Cell Lung CA | 0 | | 0 | | 60 | N,C | 40 | 60 | 60 |
| 51 | Non-Small Cell Lung CA | 0 | | 20 | C,N | 80 | N,C | 0 | 120 | 40 |
| 52 | Non-Small Cell Lung CA | 0 | | 0 | | 0 | | 100 | 0 | 0 |
| 53 | Non-Small Cell Lung CA | 0 | | 50 | C,N | 50 | C,N | 0 | 150 | 100 |
| 54 | Pancreatic CA | 70 | C,N | 30 | C,N | 0 | | 0 | 270 | 210 |
| 55 | Pancreatic CA | 20 | N,C | 70 | C,N | 10 | C,N | 0 | 210 | 60 |
| 56 | Pancreatic CA | 0 | | 0 | | 0 | | 100 | 0 | 0 |
| 57 | Pancreatic CA | 70 | C,N | 30 | C,N | 0 | | 0 | 270 | 210 |
| 58 | Pancreatic CA | 0 | | 70 | C,N | 30 | C,N | 0 | 170 | 140 |
| 59 | Pancreatic CA | 0 | | 10 | C,N | 90 | C,N | 0 | 110 | 20 |

TABLE 1-continued

|   | Tissue Type | 3+ | Sub. | 2+ | Sub. | 1+ | Sub. | 0 | H-score L | S |
|---|---|---|---|---|---|---|---|---|---|---|
| 60 | Pancreatic CA | 0 | | 0 | | 0 | | 100 | 0 | 0 |
| 61 | Pancreatic CA | 70 | C,N | 30 | C,N | 0 | | 0 | 270 | 210 |
| 62 | Pancreatic CA | 0 | | 0 | | 0 | | 100 | 0 | 0 |
| 63 | Pancreatic CA | 20 | C,N | 30 | C,N | 50 | C,N | 0 | 170 | 60 |
| 64 | Pancreatic CA | 5 | C,N | 35 | C,N | 60 | C,N | 0 | 145 | 15 |
| 65 | Pancreatic CA | 0 | | 10 | C,N | 90 | C,N | 0 | 110 | 20 |
| 66 | Pancreatic CA | 0 | | 0 | | 0 | | 100 | 0 | 0 |
| 67 | Pancreatic CA | 50 | C,N | 40 | C,N | 10 | C,N | 0 | 240 | 150 |
| 68 | Pancreatic CA | 0 | | 50 | C,N | 50 | C,N | 0 | 150 | 100 |
| 69 | Pancreatic CA | 0 | | 0 | | 0 | | 100 | 0 | 0 |
| 70 | Pancreatic CA | 0 | | 30 | C,N | 70 | C,N | 0 | 130 | 60 |
| 71 | Sarcoma | 20 | C | 40 | C | 20 | C | 20 | 200 | 60 |
| 72 | Sarcoma | 0 | | 30 | C | 70 | C,N | 0 | 130 | 60 |
| 73 | Sarcoma | 80 | C | 10 | C | 10 | C | 0 | 270 | 240 |
| 74 | Sarcoma | 0 | | 20 | C | 80 | C,N | 0 | 120 | 40 |
| 75 | Sarcoma | 0 | | 30 | C | 70 | C,N | 0 | 130 | 60 |
| 76 | Sarcoma | 30 | C | 40 | C,N | 30 | C,N | 0 | 200 | 90 |
| 77 | Sarcoma | 20 | C,N | 20 | C | 50 | C | 10 | 150 | 60 |
| 78 | Sarcoma | 0 | | 0 | | 90 | C,N | 10 | 90 | 90 |
| 79 | Synovial Sarcoma | 0 | | 0 | | 70 | C,N | 30 | 70 | 70 |
| 80 | Synovial Sarcoma | 0 | | 80 | C | 20 | C,N | 0 | 180 | 160 |
| 81 | Glioblastoma Multiforme | 0 | | 0 | | 90 | C[1] | 10 | 90 | 90 |
| 82 | Glioblastoma Multiforme | 0 | | 70 | C | 15 | C | 15 | 155 | 140 |
| 83 | Glioblastoma Multiforme | 0 | | 0 | | 0 | | 100 | 0 | 0 |
| 84 | Glioblastoma | 0 | | 0 | | 0 | | 100 | 0 | 0 |
| 85 | Glioblastoma Multiforme | 0 | | 0 | | 0 | | 100 | 0 | 0 |
| 86 | Glioblastoma Multiforme | 0 | | 0 | | 0 | | 100 | 0 | 0 |
| 87 | Glioblastoma Multiforme | 0 | | 0 | | 10 | C | 90 | 10 | 10 |
| 88 | Glioblastoma Multiforme | 5 | N,C | 5 | N,C | 85 | C | 5 | 110 | 15 |
| 89 | Glioblastoma Multiforme | 0 | | 0 | | 0 | | 100 | 0 | 0 |
| 90 | Glioblastoma Multiforme | 0 | | 0 | | 85 | C | 15 | 85 | 85 |
| 91 | Glioblastoma Multiforme | 0 | | 20 | C,N | 70 | N,C | 10 | 110 | 40 |
| 92 | Glioblastoma Multiforme | 0 | | 0 | | 0 | | 100 | 0 | 0 |
| 93 | Glioblastoma Multiforme | 0 | | 0 | | 0 | | 100 | 0 | 0 |
| 94 | Glioblastoma Multiforme | 60 | N,C | 20 | N,C | 20 | N,C | 0 | 240 | 180 |
| 95 | Glioblastoma Multiforme | 40 | N,C | 30 | N,C | 15 | C | 15 | 195 | 120 |
| 96 | Astrocytoma | 0 | | 0 | | 70 | C,N | 30 | 70 | 70 |
| 97 | Astrocytoma | 20 | N | 20 | N | 30 | N | 30 | 130 | 60 |
| 98 | Anaplastic Astrocytoma | 0 | | 0 | | 0 | | 100 | 0 | 0 |
| 99 | Astrocytoma | 0 | | 0 | | 0 | | 100 | 0 | 0 |
| 100 | Astrocytoma | 0 | | 0 | | 0 | | 100 | 0 | 0 |
| 101 | Astrocytoma | 0 | | 0 | | 0 | | 100 | 0 | 0 |
| 102 | Anaplastic Astrocytoma | 0 | | 0 | | 0 | | 100 | 0 | 0 |
| 103 | Astrocytoma | 0 | | 0 | | 5 | N,C | 95 | 5 | 5 |
| 104 | Glioblastoma Multiforme | 0 | | 0 | | 0 | | 100 | 0 | 0 |
| 105 | Astrocytoma | 0 | | 0 | | 0 | | 100 | 0 | 0 |
| 106 | Glioblastoma Multiforme/Spindle Cell Type | 0 | | 0 | | 15 | N,C | 85 | 15 | 15 |
| 107 | Anaplastic Astrocytoma | 0 | | 0 | | 60 | N | 40 | 60 | 60 |
| 108 | Anaplastic Astrocytoma | 0 | | 0 | | 0 | | 100 | 0 | 0 |
| 109 | Astrocytoma | 0 | | 0 | | 0 | | 100 | 0 | 0 |
| 110 | Anaplastic Astrocytoma | 0 | | 0 | | 0 | | 100 | 0 | 0 |
| 111 | Anaplastic Astrocytoma | 0 | | 0 | | 50 | N | 50 | 50 | 50 |
| 112 | Anaplastic Astrocytoma | 0 | | 0 | | 50 | N | 50 | 50 | 50 |
| 113 | Anaplastic Astrocytoma | 0 | | 0 | | 0 | | 100 | 0 | 0 |
| 114 | Anaplastic Astrocytoma | 0 | | 10 | N | 80 | N | 10 | 100 | 20 |
| 115 | Anaplastic Astrocytoma | 0 | | 0 | | 0 | | 100 | 0 | 0 |
| 116 | Anaplastic Astrocytoma | 0 | | 0 | | 0 | | 100 | 0 | 0 |
| 117 | Anaplastic Astrocytoma | 0 | | 0 | | 0 | | 100 | 0 | 0 |
| 118 | Anaplastic Astrocytoma | 0 | | 0 | | 0 | | 100 | 0 | 0 |
| 119 | Glioblastoma Multiforme | 5 | N | 5 | N | 10 | N | 80 | 35 | 15 |
| 120 | Glioblastoma Multiforme | 0 | | 0 | | 0 | | 100 | 0 | 0 |
| 121 | Astrocytoma | 0 | | 0 | | 0 | | 100 | 0 | 0 |
| 122 | Glioblastoma Multiforme | 0 | | 0 | | 0 | | 100 | 0 | 0 |
| 123 | Glioblastoma | 5 | N,C | 50 | C,N | 15 | C,N | 30 | 130 | 15 |
| Cn | NSC Lung CA | 80 | M,C,N | 15 | M,C,N | 5 | M,C | 0 | 275 | 240 |
| Cn | Cell Line A427 | 20 | N,C,M | 15 | N,C,M | 5 | C | 60 | 95 | 60 |
| Cn | NSC Lung CA | 0 | | 0 | | 0 | | 100 | 0 | 0 |
| Cn | Cell Line A549 | 0 | | 0 | | 0 | | 100 | 0 | 0 |

"C" indicates cytoplasmic staining, "M" indicates membrane staining, "N" indicates nuclear staining, "L" stands for long, "S" stands for short and "Cn" indicates control. The percent of positively staining cells from 0–3+ is given for the distinctive tissue element.

VI. Administration of Drugs Directed to MTAP Deficient Cancers

Using the assays described herein to determine the MTAP status of a cancer, mammalian hosts (e.g., humans) suffering from an MTAP deficient cancer may be treated with a therapeutically effective dose of drug, combinations of drugs, or drug and/or drugs and other cancer therapies (for example, radiation) determined to be of use in treating MTAP deficient cancers. One preferred class of drugs for treating MTAP deficient cancers are drugs that inhibit de novo purine synthesis, including IMPDH inhibitors. Examples of such drugs are, without limitation, L-alanosine, 10-propargyl-10-deazaminopterin (PDX), N-(4-(((2,4-diamino-6-pteridinyl)methyl)methylamino)benzoyl)-L-glutamic acid) (methotrexate), AG2037 (Agouron/Pfizer), 4-aminopteroylglutamic acid (aminopterin), 2,4-diamino-5-methyl-6-[[(3,4,5-trimethoxyphenyl)amino]methyl]quinazoline (trimetrexate), pyritrexim, 10-ethyl-deaza-aminopterin (edatrexate), 4'-methylene-10-deazaminopterin (MDAM), 10-propargyl-5,8-dideazafolic acid (PDDF), N-[5-[N-(3,4-dihydro-2-methyl-4-oxoquinazolin-6-ylmethyl)-N-methylamino]-2-thenoyl-L-glutamic acid (raltitrexed; ZD1694, Tomudex), N-[4-[2-(2-amino-3,4-dihydro-4-oxo-7H-pyrrolo[2,3-d]-pyrimidin-5-yl)ethyl]-benzoyl]-L-glutamic acid (LY231514; Lilly), 6-(2'-formyl-2'naphthyl-ethyl)-2-amino-4(3H)-oxoquinazoline (LL95509), (6R,S)-5,10-dideazatetrahydrofolic acid (DDATHF), 4-[2-(2-amino-4-oxo-4,6,7,8-tetrahydro-3Hpyrimidino[5,4,6][1,4]-thiazin-6yl)-(S)-ethyl]-2,5-thienoylamino-L-glutamic acid (AG2034), and N-[5-(2-[(2,6-diamino-4(3H)-oxopyrimidin-5-yl)thio]ethyl)thieno-2-yl]-L-glutamic acid (AG2009), 6R2',5'thienyl5,10-dideazatetrahydrofolic acid (LY309887), (S)-2-[4-[N-[(3,4-dihydro-2,7-dimethyl-4-oxo-6-quinazolinyl)methyl]-N-prop-2-ynylamino]-2-fluorob enzamido]-4-(1H-1,2,3,4-tetrazol-5-yl)butyric acid (ZD9331), N-[4-[N-[(3,4-dihydro-2,7-dimethyl-4-oxo-6-quinazolinyl)methyl]-N-prop-2-ynylamino]-2-fluorob enzoyl]-L-glutamic acid (ZM214888), N(alpha)-[4-[5-(2,4-diaminoteridin-6-yl)pent-1-yn-4-yl]benzoyl]-N(delta)-hemiphthaloyl-L-ornithine, or N(alpha)-(4-amino-4-deoxypteroyl)-N(delta)-hemiphthaloyl-L-ornithine (PT523).

A preferred MTAP therapy regimen included in the scope of the invention is the use of "rescue" agents in combination with de novo purine synthesis inhibitors. Rescue agents protect normal MTAP positive cells from exposure to cancer drugs that are de novo purine synthesis inhibitors. For example, non-malignant, MTAP competent cells may be protected from any effect of exposure to de novo purine synthesis inhibitors through administration of MTA or a suitable substrate analogue for use in adenine synthesis. Suitable compounds for use in this regard include MTA, 2'-5'-dideoxyadenosine, 5'-deoxyadenosine, 2'-deoxy-5-deoxy-5'methylthioadenosine. It will be appreciated, however, that MTAP competent cells are capable of producing adenine from metabolism of methylthioadenosine for replenishment of the AMP cellular pool and therefore would not be expected to be depleted of AMP to the same extent as MTAP deficient cells.

VII. Uses

The present invention provides reagents which will find use in diagnostic applications as described elsewhere herein, or below in the description of kits for diagnosis.

Antibodies and other MTAP-binding agents directed towards human MTAP protein may be used to purify the corresponding MTAP protein. Antibodies and other MTAP-binding agents may also be used in a diagnostic fashion to determine whether MTAP protein is present or absent in a tissue sample or cell population using the methods described herein. Also, many cancers are associated with a deletion of the gene encoding the MTAP protein, and therapies directed to MTAP deficient tumor cells are presently under development. Thus, the MTAP-binding agents and methods described herein have use in identifying patients who would benefit from treatments designed to target MTAP deficient cancers. Further, because many cancers with deletions of the gene encoding MTAP also have deletions of the genes encoding p14 and p16, the identification of MTAP deficient cells can be used as a surrogate marker for deletion of p14 and p16. Tumors with deletions of the genes encoding p14, p16, and MTAP are associated with advanced stage tumors. Still further, because some cancers initially start off as MTAP positive but later become MTAP negative, that MTAP-binding agents described herein have use in monitoring tumor progression.

VIII. Kits

This invention also includes the use of the antibodies of the invention in a variety of diagnostic kits and methods for detecting the presence or absence of human MTAP protein in a biological sample.

A kit for determining the presence (high, normal or low expression) or absence of human MTAP protein in a sample would typically comprise an MTAP-binding agent, e.g., antibody, having known binding affinity for the human MTAP protein. Compartments containing reagents, and instructions, will normally be provided.

Frequently, the reagents for diagnostic assays are supplied in kits, so as to optimize the sensitivity of the assay. For the subject invention, depending upon the nature of the assay, the protocol, and the label, either labeled or unlabeled MTAP-binding agent may be included. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Many of the aforementioned constituents of the diagnostic assays may be used without modification or may be modified in a variety of ways. For example, labeling may be achieved by covalently or non-covalently joining a moiety that directly or indirectly provides a detectable signal. In many of these assays the MTAP-binding agents, e.g., antibodies can be labeled either directly or indirectly. Possibilities for direct labeling include label groups such as radiolabels, e.g., $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

The MTAP protein can be immobilized on various matrices followed by washing. Suitable matrices include plastic such as an ELISA plate, filters, and beads. Methods of immobilizing the MTAP protein to a matrix include, without limitation, direct adhesion to plastic, use of a capture antibody, chemical coupling, and biotin-avidin. The last step in this approach involves the precipitation of protein/antibody complex by one of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Another diagnostic aspect of this invention involves use of the MTAP-binding agents of the invention in conjunction with oligonucleotide or polynucleotide probes based on the sequence of the polynucleotide encoding human MTAP protein. The probes can be used for detecting polynucleotides that encode the MTAP protein from samples of patients suspected of having an abnormal condition, e.g., cancer. The preparation of both RNA and DNA nucleotide sequences, the labeling of the sequences, and the preferred size of the sequences has been discussed herein and in the literature. Normally an oligonucleotide probe should have at least about 14 nucleotides, usually at least about 18 nucleotides, and the polynucleotide probes may be up to several kilobases. Preferred oligonucleotide probes to detect for the presence or absence of polynucleotides encoding MTAP protein include probes that detect exons 4, 5, or 8, or combinations of all three.

Diagnostic kits that also test for the qualitative or quantitative presence of other markers are also contemplated. Diagnosis or prognosis may depend on the combination of multiple indications used as markers. Thus, kits may test for combinations of markers, e.g., MTAP, p16, p14$^{ARF}$. Such kits may contain a combination of reagents, for example, binding agents specific for MTAP, p16, or p14$^{ARF}$, oligonucleotide probes specific for the polynucleotides that encode MTAP, p16, p14$^{ARF}$, or combinations of all the aforementioned. The cDNA sequence for MTAP is shown in SEQ ID NO:2. The cDNA and protein sequences for p16 and p14$^{ARF}$ are shown in SEQ ID NOS:3 through 10.

For detection of the presence or absence of human MTAP, an immunohistochemical staining procedure can be employed that utilizes an MTAP-binding agent that selectively binds to human MTAP. The sample to be screened can be embedded in a paraffin block or similar embedding material prior to the time the kit is used. Further, if the sample is not tissue but blood, plasma, or lymph, the sample can be fixed to a suitable surface, such as glass prior to the time the kit is used.

Although the invention is described herein using anti-human MTAP monoclonal antibodies, those skilled in the art will understand that it is also applicable to any antagonist, which recognize the target molecule to be detected. Any antagonist including antigens, primers, nucleic acids, or fragments thereof, that recognize specific proteins, markers, receptors or antibodies, or fragments thereof, to be detected may be used. Therefore, one skilled in the art using the teachings disclosed herein can develop the conditions necessary to detect the presence or absence of human MTAP in an embedded tissue for other MTAP-binding agents, such as polyclonal antibodies.

IX. Deposits

Hybridoma cell line 6.9 was deposited on Feb. 11, 2003, with the American Type Culture Collection (ATCC), 10801 University Boulevard, Va. 20110-2209 U.S.A and given ATCC patent deposit designation number PTA-5001.

Applicants' assignee, Salmedix, Inc. represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR § 1.14, and 35 USC § 122. The deposited material will be maintained with all the care necessary to keep it viable and uncontaminated for a period of at least five years after the most recent request for the furnishing of a sample of the deposited antibody, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

To assist in understanding, the present invention will now be further illustrated by the following examples. These examples as they relate to this invention should not, of course, be construed as specifically limiting the invention and such variations of the invention, now known or later developed, which would be within the purview of one skilled in the art are considered to fall within the scope of the invention as described herein and hereinafter claimed.

EXAMPLES

Example 1

Cloning of Human MTAP cDNA

Total RNA was isolated from A427 cells (obtained from American Type Culture Collection; Rocville, Md.) with RNA STAT-60™ (Tel-Test B, Inc., Friendswood, Tex.) and transcribed to cDNA using a Superscript preamplification system (Life Technologies). MTAP cDNA was amplified using the polymerase chain reaction (PCR). Primers used for the amplification of MTAP were: sense 5'-CTC GCC CAC TGC AGA TTC CTT TCC CGT-3' (SEQ ID NO:11); antisense: 5'-GGC AGC CAT GCT ACT TTA ATG TCT TGG-3' (SEQ ID NO:12).

The PCR amplification was carried out in a 25 µl reaction mixture containing 1 µg of transcribed cDNA, 1×PCR buffer [10 mM Tris-HCl (pH 8.0), 50 mM KCl, 1.5 mM MgCl$_2$, and 0.0001% gelatin], 400 µM of each deoxynucleoside triphophate, 50 ng each of sense and antisense primers, and 2.5 units of Taq polymerase (Strategene, La Jolla, Calif.). Thirty cycles were performed with the programmable cyclic reactor (GeneAmp PCR system 9600; Perkin Elmer, Norwalk, Conn.). Each cycle consists of denaturation at 94° C. for 1 min, annealing at 55° C. for 1 min, and extension at 72° C. for 1 min.

The MTAP cDNA was inserted into the expression vector pQE-32 (Qiagen). The orientation of the insert was determined by digesting plasmid DNA with HindIII.

Example 2

Expression and Purification of Human MTAP Protein

The protein was purified as follows using the QIAexpress Expression System (Qiagen): *E. coli* strain M15[pREP4] was transformed with plasmid pQE-32 carrying human MTAP cDNA, and grown in 3L LB medium containing 100 µg/ml ampicillin and 25 µg/ml kanamycin with shaking until an OD$_{600}$ of 0.434 was reached. Then, IPTG (isopropyl-beta-D-thiogalactopyranoside) was added to a final concentration of 2 mM and the culture was grown at 37° C. with shaking for 5 hours. The cells were harvested by centrifugation at 4000×g for 20 min. The bacterial cell pellet was resuspended with 30 ml sonication buffer [50 mM $NaH_2PO_4$ pH 8.0, 300 mM NaCl, 10 mM 2-mercaptoethanol, and 1 mM phenylmethylsulfonyl fluoride (PMSF)] and incubated on ice for 30 min. The suspension was frozen in liquid $N_2$ and stored overnight at −80° C.

The sample was thawed on ice and sonicated for 2–5 minutes with a 50% pulse using a Branson Sonifier 450 Sonicator. The sample was then centrifuged at 30,000 g for 30 min and the supernatant collected and filtered with a 0.2 μm filter (Corning). To the filtrate was added 20 ml Ni-NTA resin (Qiagen) that had been pre-equilibrated with sonication buffer. This was mixed at 4° C. for 60 min and loaded onto a $Ni^{2+}$ nitriloacetic acid agarose column. The flowthrough was loaded onto the column again. The column was washed with 100 ml sonication buffer at a flow rate less than 0.5 ml/min until the flow through $OD_{280}$ was less than 0.01 ml/min. The column was washed with 160 ml wash buffer [50 mM $NaH_2PO_4$ pH 5.9, 1 M NaCl, 1 mM PMSF, 10% glycerol]. Bound protein was eluted with 20 ml sonication buffer containing 0.5 M imidazole. The imidazole was removed and the protein concentrated using a Centriprep 10 (Amicon).

Example 3

Hybridoma and Monoclonal Antibody Production

A. General Methods and Materials
 1. Materials
 Cell Culture Medium
DME-HY:

| | |
|---|---|
| DMEM with 4.5 g glucose/L (Sigma HybriMax ®) | 350 ml |
| Fetal Bovine Serum (Hyclone Characterized or better) | 100 ml |
| NCTC 109 medium (Sigma N-1140 or equivalent) | 50 ml |

100×OGI solution:

| | |
|---|---|
| (3 mM Oxaloacetic Acid, Sodium Salt [Sigma HybriMax ®], ~6–7 units/ml Bovine Insulin [Sigma HybriMax ®], 9.2 μM Glycine [Sigma G-7126]. | 5 ml |
| 100X L-Glutamine Solution (200 mM, Sigma HybriMax ®) | 5 ml |

DME-HAT:

10 ml of 50×HAT supplement (Sigma HybriMax®) in 500 ml DME-HY

DME-HT:

10 ml of 50×HT supplement (Sigma HybriMax®) in 500 ml DME-HY

ELISA REAGENTS:
1. Carbonate-Bicarbonate Coating Buffer Capsule (Sigma).
2. Affinity purified, AP conjugated goat-anti-mouse antibody (KPL, Gaithersburg, Md.)
3. p-Nitrophenol Phosphate (PNPP) substrate (Sigma, 20 mg/tab)
4. Dynex Immulon-4 plates: 96-well plates, or 12-well removawell® strips and holder frame (Dynex, Chantilly, Va.).
5. Developing buffer: 1 M Diethanolamine (Fisher), 0.5 mM $MgCl_2$, pH 9.8.
6. Screening ELISA plate preparation: Purified recombinant MTAP protein (500 ng/well) was adsorbed onto microtiter plates in sodium carbonate/bicarbonate buffer overnight at 4° C., then blocked for nonspecific binding with phosphate-buffered saline (PBS) buffer containing 1% bovine serum albumin (BSA). After blocking the plates were stored at −20° C. until use.

2. Methods
 a. ELISA

Diluted antiserum was added onto ELISA plates and incubated for 1 hr at room temperature. After incubation, the plates were washed 3 times with PBS to remove any unbound serum proteins. Alkaline-phosphatase conjugated anti-mouse secondary antibody was added to the plates, and incubation was continued at room temperature for 1 hr. At the end of the secondary antibody incubation, 3 washes with PBS were performed to remove non-specific secondary antibody. Then, the calorimetric substrate (p-nitrophenyl phosphate, PNPP) was added and the plates were analyzed after 5–30 min with a microtiter plate reader.

b. Western blotting

Recombinant MTAP protein (as described herein) was fractionated by 12% sodium dodecyl sulfate polyacrylamide gel electrophoresis (SDS-PAGE) and transferred onto a 0.22 μm-nitrocellulose membrane. After blotting, the membrane was blocked in Tris-buffered saline-Tween20 buffer (TBST) plus 5% non-fat dry milk (TBST-M) for 30 min at room temp. To determine the antibody specificity, antiserum was diluted in TBST-M and added to the nitrocellulose membrane. After 1 hr incubation at room temp, unbound antibody and serum proteins were removed by 3 washes with TBST. Alkaline-phosphatase (AP) conjugated anti-mouse secondary antibody was added to the membrane for additional 1 hour incubation and the protein signal was visualized by adding the AP substrate BCIP/NBT.

B. Hybridoma Fusion and Isolation

A total of 5 mice were immunized with the human MTAP protein produced above (including the His tag). Initially, each animal received 50 μg of purified recombinant protein mixed with complete Freund's adjuvant (CFA) by subcutaneous injection. Subsequent "boost" immunizations, using the same amount of antigen in incomplete Freund's adjuvant (IFA), were performed at 2-week intervals for a total of 4 boosts. After a total of 5 injections, the best responding mouse (as determined by analysis of polyclonal antiserum, as described below) was used for monoclonal antibody production.

1. Polyclonal Antiserum Analysis

Five days after the second boost injection and each subsequent injection, the blood from each immunized mouse was collected by nicking the vein behind the eye. Polyclonal antiserum was prepared by using a microtainer® spin column (Becton Dickinson) to separate the blood cells. The titer for specific polyclonal antibodies was monitored primarily by screening the antiserum by enzyme-linked immunosorbent assay (ELISA), as described above, and the specificity of the antiserum was determined by Western blotting with recombinant protein.

The best responding mouse (based on anti-MTAP polyclonal antisera titer determined by ELISA) was given an additional immunization, without adjuvant, which was delivered by tail vein injection. Three days after the final injection, the mouse was sacrificed and the splenocytes were collected for hybridoma fusion as described herein.

2. Hybridoma Fusion

Hybridoma cells were generated by the polyethylene glycol (PEG)-mediated cell fusion method. All solutions were pre-warmed to 37° C. immediately prior to the fusion. Splenocytes from the immunized mouse and myeloma NS1 cells were collected by centrifugation and washed three times with DMEM. After the final wash, cells were combined in one tube and any trace amount of DMEM was removed by aspiration without disturbing the cell pellet. One milliliter of 50% PEG solution was added in a drop-wise fashion to the cell pellet over a one-minute interval with constant mixing. After an additional minute of stirring, two milliliters of DMEM were gradually added to the cell mixture over a two-minute period with constant mixing, and then seven milliliters of DME-HY were added slowly over a three minute period to stop the fusion reaction. The fusion cells were collected by low-speed centrifugation and then resuspended in DME-HAT and plated out onto 96-well plates at 200 µl per well.

3. Monoclonal Antibody Screening

After 12–14 days of HAT selection the resulting hybridoma supernatants were screened primarily by ELISA, as described above, for reactivity with plates that had been previously coated with recombinant protein. Initially, 25 ELISA-positive clones were identified. These clones were propagated in DME-HT media and retested by ELISA to confirm the positive result and to eliminate any false-positive clones from the primary screen. After secondary screening, a total of 16 ELISA-positive hybridomas were identified. These positive hybridoma clones were expanded further in DME-HY media and the cells were preserved in liquid nitrogen for future single-cell cloning. The supernatants from these cultures were collected for further screening and characterization, as described below.

To check the specificity of the antibodies, lysates from MTAP-expressing cells (the leukemia MOLT-4 [ATCC] and the lung cancer A427 [ATCC]) and MTAP-deleted cells (the leukemia JURKAT [ATCC] and the lung cancer A549 [ATCC]) were immunoblotted onto PVDF or nitrocellulose membranes. The membranes were incubated with the supernatants from the hybridoma cultures (diluted 1:2 and 1:10) and the reactive bands were revealed by chemiluminescence using secondary anti-mouse antibody conjugated to horseradish peroxidase (HRP) followed by incubation with chemiluminescent substrate. An MTAP-specific antibody would reveal an MTAP band at an approximate molecular weight of 30–35 kDa only in the MOLT-4 and A427 lanes, but not in the lanes containing JURKAT or A549 lysates. Using whole cell lysates to identify MTAP-specific antibodies has the advantage of allowing the detection of possible cross-reactivity with unrelated proteins. The best supernatant identified using this screening was clone 6.

4. Single Cell Cloning

Clone 6 was selected for single-cell cloning to generate anti-MTAP monoclonal antibodies. Parental hybridoma cells from clone 6 were grown from frozen stock and the supernatant was collected and tested again by ELISA. The serial-dilution method was used for single-cell cloning. Briefly, hybridoma cells were counted and plated out onto a total of ten 96-well plates at a concentration of 1, 0.5, and 0.1 cells per well. Clones grown from a single cell were initially screened again by ELISA against purified MTAP protein, and then tested by immunoblotting in MTAP-expressing and MTAP-deleted cells, as described above to ensure the antibody's specificity and reactivity as seen with the parental hybridoma. A total of 4 sub-clones derived from the parental clone 6 were chosen after screening by Western blot analysis (clones 6.9, 6.11, 6.22 and 6.23) (FIG. 1). Each of these four sub-clones was expanded in culture to a larger quantity and then frozen in liquid nitrogen to preserve the antibody producing cell line. The tissue culture supernatant was collected for final testing using the described immunoblotting technique. Clone 6.9 was identified as having acceptable properties. It strongly recognized the MTAP band at the expected molecular weight, only in the MTAP-expressing cells MOLT-4 and A427, but not in the MTAP-deleted cells JURKAT and A549. It displayed a high specificity with low background and little cross-reaction with non-specific bands.

5. Monoclonal Antibody Purification

Tissue culture supernatant was collected from clone 6.9 and the anti-MTAP monoclonal antibody was purified by protein G-affinity chromatography. Briefly, the supernatant was cleared of cellular debris by high-speed centrifugation followed by ultra-filtration (0.22 µm filter) before being loaded onto a protein-G column. After antibody binding, the column was washed with PBS to remove any non-specific antibody and unbound proteins that were present in the supernatant. The anti-MTAP monoclonal antibody was eluted by 0.1 M glycine solution (pH 2.8) and the antibody-containing fractions were pooled and dialyzed extensively against PBS at 4° C. The final purified antibody concentration was determined by UV (280 nm) absorbance.

Example 4

Immunohistochemistry

A. Reagents and Controls

Mouse monoclonal anti-MTAP antibody, clone 6.9, of human $IgG_1$ isotype was stored at −85° C. at a stock concentration of 3.3 mg/ml. Aliquots of the monoclonal antibody were stored at 2–8° C. for up to four weeks.

Negative control for the mouse monoclonal anti-MTAP antibody was mouse $IgG_{1\kappa}$ (Sigma-Aldrich). The antibody was received on dry ice at a stock concentration of 1 mg/ml, and aliquots were stored at −20° C. Aliquots of 40 µl were stored at −20° C. When thawed, they were stored at 2–8° C. for up to one week.

Because MTAP is present in all normal tissues, the ideal control tissue would be one in which the gene had been deleted. Research suggested that a significant percentage of non-small cell carcinoma cases have a deleted MTAP gene and thus would be expected to be negative in an MTAP immunohistochemistry assay. As controls, two non-small cell carcinomas were selected: one in which MTAP was present in the cells and detected via immunohistochemistry; and one in which MTAP was deleted from the cells and not detected via immunohistochemistry. An additional positive control included MTAP-expressing human non-small cell lung carcinoma A427 (ATCC) embedded in a paraffin block. The MTAP-deleted human non-small cell lung carcinoma A549 (ATCC), paraffin embedded, was also used as another negative tissue control.

The negative reagent control is a species- and isotype-matched antibody run at the same concentration on the same tissues as the primary antibody.

B. Methods

1. Test System

Fixed, paraffin-embedded human tissue specimens, obtained from surgery or autopsy were used. The specimens were cut at 5 microns, placed onto positively-charged glass slides (Fisher Scientific), air-dried, and stored at room temperature until needed. The specimens examined were: 42 non-small cell lung cancer, 17 pancreatic cancer, 8 sarcoma, 5 leiomyosarcoma, 2 liposarcoma, 1 osteorsarcoma, 2 synovial sarcoma, 3 glioma, 20 glioblastoma, and 22 astrocytoma.

2. Pretreatment

A pretreatment analysis was performed using non-small cell lung carcinoma as the tissue control and the positive and negative control cell lines. In this analysis, the following pretreatments were tested using 10 μg/ml of the mouse monoclonal MTAP antibody:

1. Untreated
2. Saponin (Sigma)
3. H.I.E.R. (Heat-Induced Epitope Retrieval; Pressure Cooker, Reveal) 120° C., 3 minutes followed by Trypsin (Sigma) 5 minutes
4. H.I.E.R. (Pressure Cooker, BORG) 120° C., 3 minutes followed by Trypsin 5 minutes
5. H.I.E.R. (Pressure Cooker, Reveal) 95° C., 60 minutes followed by Trypsin 5 minutes
6. H.I.E.R. (Pressure Cooker, BORG) 95° C., 60 minutes followed by Trypsin 5 minutes
7. H.I.E.R. (Pressure Cooker, BORG) 120° C., 3 minutes followed by Trypsin 1 minute, 30 minutes Ab incubation
8. H.I.E.R. (Pressure Cooker, BORG) 120° C., 3 minutes followed by Trypsin 1 minute, 1 hour Ab incubation
9. H.I.E.R. (Pressure Cooker, Reveal) 120° C., 3 minutes followed by Trypsin 1 minute, 2 hour Ab incubation As a result of the pretreatment analysis, H.I.E.R. (Pressure Cooker, BORG) at 120° C. for 3 minutes followed by trypsin for one minute was selected as a suitable pretreatment and used for the remainder of the study.

3. Titration

For the detection of overexpression of an antigen, the MTAP binding-agent titer is selected as the lowest concentration that produces the highest combination of staining intensity and percentage of positively staining cells while minimizing background staining. Since the purpose of the assay is to detect the absence of a protein as the result of a gene deletion, a higher titer of MTAP-binding agent was selected to minimize possible false negatives. A suitable titer for this test was selected as the highest concentration of antigen binding agent that produces strongest staining while minimizing isotype and stromal background staining.

A titration analysis was performed with the mouse anti-MTAP monoclonal antibody on fixed, paraffin-embedded specimens. Initially, five-serial dilutions (20 μg/ml, 10 μg/ml, 5 μg/ml, 2.5 μg/ml, 1.25 μg/ml) were tested on the positive and negative cell line controls as well as the tissue control (placenta). Using a non-small cell carcinoma cell line deleted for MTAP, a titration analysis was performed using five-serial dilutions (80 μg/ml, 40 μg/ml, 20 μg/ml, 10 μg/ml, and 5 μg/ml). Based on these studies, a primary antibody (and negative reagent control) titer of 20 μg/ml was selected for the remainder of the study.

4. Immunohistochemistry

All immunohistochemical testing for the mouse monoclonal MTAP antibody was performed using the Mouse EnVision+™ Kit (DAKO Corporation, Carpinteria, Calif.) according to manufacturer's instructions. For paraffin-embedded specimens, slides containing microtome-cut sections were removed from incubation in a 60° C. oven after at least 60 minutes and cooled to room temperature. The slides were deparaffinized in xylene and graded alcohols, rinsed in running water, and rinsed three times in deionized water. For H.I.E.R., the slides were then incubated in a pressure cooker (BORG) at 120° C. for 3 minutes followed by trypsin for one minute, and were then washed three times in PBS (Phosphate-Buffered Saline; DAKO Corp.). Endogenous peroxidase activity was blocked with a 5-minute incubation in a hydrogen peroxide solution contained in the EnVision+™ Kit, followed by three PBS washes. The slides were then incubated with the primary antibody (or the appropriate negative reagent control) at 20 μl/ml for 30 minutes at room temperature. The slides were washed three times in PBS and incubated with Labeled Polymer from the EnVision+™ Kit for 30 minutes at room temperature. Following three PBS washes, the peroxidase reaction was visualized by incubating with 3,3',-diaminobenzidine tetrahydrochloride solution (DAKO Corp.) for five minutes. Tissue sections were thoroughly washed with tap water, counterstained with Harris hematoxylin solution (mercury free) (Fisher-cat. No. 245-678), dipped in 0.25% acid alcohol, blued in 0.2% ammonia, dehydrated through graded alcohols, cleared in xylene, and coverslipped.

Interpretation of stained slides was performed as described herein. The scoring system included an analysis of staining intensity. The staining intensity of the test article was judged relative to the intensity of a control slide containing an adjacent section stained with a negative control antibody. Staining of the section labeled with the negative reagent control was considered. "background." A "0" indicates no staining relative to background. A "1+" indicates weak staining. A "2+" indicates moderate staining, and a "3+" indicates strong staining (see, Table 1). Staining intensity was reported at the highest level of intensity observed in all tissue elements, except the distinctive tissue element where an expanded scoring scheme was reported. Descriptive statistics were performed using Microsoft Excel as described herein.

C. Results

For all results (Table 1), "C" indicates cytoplasmic staining, "M" indicates membrane staining, and "N" indicates nuclear staining. The percent of positively staining cells from 0–3+is given for the distinctive tissue element (Table 1).

The data shown in Table 1 agree with previously reported data obtained in the same tumor types using hybridization based techniques to detect the presence or absence of the MTAP gene at the DNA or RNA levels.

When three anti-MTAP antibodies to human MTAP (clone 6.9, and purified and unpurified versions of a chicken polyclonal antibody) were tested on frozen human tissues embedded in OCT compound using an indirect immunohistochemical technique, the antibodies performed poorly.

Example 5

Determination of the Epitope Overlap of Antibodies Against Human MTAP Protein or Fragments Thereof A competitive enzyme immunoassay is carried out to detect the epitope overlap of an antibody with the monoclonal antibody produced by hybridoma cell line ATCC PTA-5001. For this assay recombinant MTAP protein, as described herein, is biotinylated with D-biotinyl-ε-amidocaproic acid-N-hydroxysuccinimide ester (Roche Diagnostics GmbH, Catalogue No. 1 008 960) according to the manufacturer's instructions. 300 ng of this biotinylated antigen is bound in a volume of 100 μl PBS to a streptavidin-coated microtiter plate (produced according to EP-A 0 344 578) by incubating for 1 hour at room temperature. After washing four times with PBS/0.05% Tween 20, it is incubated simultaneously for 90 minutes at room temperature with monoclonal antibody 6.9, which is labeled with peroxidase (final concentration 250 mU/ml) and with the antibody to be assessed. After washing again four times with PBS/0.05% Tween 20, it is incubated for 30 minutes at room temperature with the enzyme-substrate solution ABT® in a buffer containing sodium perborate and subsequently the absorbance at 405 nm is measured as a measure for the amount of bound POD-labeled monoclonal antibody 6.9. This value is compared with the absorbance that is obtained when monoclonal antibody 6.9 is incubated alone. When competition of at least 50% is detectable at a $10^5$-fold excess of the antibody to be assessed in relation to monoclonal antibody 6.9 enzyme-conjugate (250 mU/ml) an epitope overlap is present.

Example 6

Mapping of anti-MTAP Monoclonal 6.9 Antibody Epitopes by ELISA and Immunoblotting Recombinant human MTAP protein is digested with various proteolytic enzymes (in individual experiments). For trypsin digestion, partial digestion of recombinant human MTAP protein is done in 50 mM Tris-HCl, 2 mM $CaCl_2$, pH 8.0 at 37° C. for 4 hr with an enzyme to substrate ratio of 1:1. The time of digestion is determined by monitoring the amount of digestion at various time points. The digestion products and controls are run on both non-reducing and reducing (as described above) SDS-PAGE. For non-reducing gels, fragments obtained after proteolytic digestion are run on 12.5% (w/v) native polyacrylamide gels. After separation, the recombinant protein and digested fragments are transferred onto a 0.22 μm-nitrocellulose membrane. Blots are probed with anti-MTAP monoclonal antibody 6.9 as described above.

Other Embodiments

The invention is not limited to those embodiments described herein, but may encompass modification and variations which do not depart from the spirit of the invention. While the invention has been described in connection with specific embodiments thereof, those of ordinary skill in the art will understand that further modifications are within the scope of the following claims. In addition, where features or aspects of the invention are described in terms of Markush groups or other grouping of alternatives, those skilled in the art will recognize that the invention is also thereby described in terms of any individual member or subgroup of members of the Markush group or genus, and exclusions of individual members as appropriate.

TABLE 2

```
Met Ala Ser Gly Thr Thr Thr Ala Val Lys Ile Gly Ile Ile Gly      SEQ. ID. NO. 1
1            5               10              15

Gly Thr Gly Leu Asp Asp Pro Glu Ile Leu Glu Gly Arg Thr Glu Lys
            20              25              30

Tyr Val Asp Thr Pro Phe Gly Lys Pro Ser Asp Ala Leu Ile Leu Gly
        35              40              45

Lys Ile Lys Asn Val Asp Cys Ile Leu Leu Ala Arg His Gly Arg Gln
        50              55              60

His Thr Ile Met Pro Ser Lys Val Asn Tyr Gln Ala Asn Ile Trp Ala
65              70              75              80

Leu Lys Glu Glu Gly Cys Thr His Val Ile Val Thr Thr Ala Cys Gly
                85              90              95

Ser Leu Arg Glu Glu Ile Gln Pro Gly Asp Ile Val Ile Ile Asp Gln
            100             105             110

Phe Ile Asp Arg Thr Thr Met Arg Pro Gln Ser Phe Tyr Asp Gly Ser
        115             120             125

His Ser Cys Ala Arg Gly Val Cys His Ile Pro Met Ala Glu Pro Phe
130             135             140

Cys Pro Lys Thr Arg Glu Val Leu Ile Glu Thr Ala Lys Lys Leu Gly
145             150             155             160

Leu Arg Cys His Ser Lys Gly Thr Met Val Thr Ile Glu Gly Pro Arg
                165             170             175

Phe Ser Ser Arg Ala Glu Ser Phe Met Phe Arg Thr Trp Gly Ala Asp
            180             185             190

Val Ile Asn Met Thr Thr Val Pro Glu Val Val Leu Ala Lys Glu Ala
        195             200             205

Gly Ile Cys Tyr Ala Ser Ile Ala Met Ala Thr Asp Tyr Asp Cys Trp
        210             215             220

Lys Glu His Glu Glu Ala Val Ser Val Asp Arg Val Leu Lys Thr Leu
```

TABLE 2-continued

```
                225                 230                 235                 240
Lys Glu Asn Ala Asn Lys Ala Lys Ser Leu Leu Leu Thr Thr Ile Pro
                    245                 250                 255
Gln Ile Gly Ser Thr Glu Trp Ser Glu Thr Leu His Asn Leu Lys Asn
                260                 265                 270
Met Ala Gln Phe Ser Val Leu Leu Pro Arg His
    275                 280
```

| | | | |
|---|---|---|---|
| gaattccgct ccgcactgct cactcccgcg cagtgaggtt ggcacagcca ccgctctgtg | 60 | SEQ. ID. NO. 2 | |
| gctcgcttgg ttcccttagt cccgagcgct cgcccactgc agattccttt cccgtgcaga | 120 | | |
| catggcctct ggcaccacca ccaccgccgt gaagattgga ataattggtg aacaggcct | 180 | | |
| ggatgatcca gaaattttag aaggaagaac tgaaaaatat gtggatactc catttggcaa | 240 | | |
| gccatctgat gccttaattt tggggaagat aaaaaatgtt gattgcatcc tccttgcaag | 300 | | |
| gcatggaagg cagcacacca tcatgccttc aaaggtcaac taccaggcga acatctgggc | 360 | | |
| tttgaaggaa gagggctgta cacatgtcat agtgaccaca gcttgtggct ccttgaggga | 420 | | |
| ggagattcag cccggcgata ttgtcattat tgatcagttc attgacagga ccactatgag | 480 | | |
| acctcagtcc ttctatgatg gaagtcattc ttgtgccaga ggagtgtgcc atattccaat | 540 | | |
| ggctgagccg ttttgcccca aaacgagaga ggttcttata gagactgcta agaagctagg | 600 | | |
| actccggtgc cactcaaagg ggacaatggt cacaatcgag ggacctcgtt ttagctcccg | 660 | | |
| ggcagaaagc ttcatgttcc gcacctgggg ggcggatgtt atcaacatga ccacagttcc | 720 | | |
| agaggtggtt cttgctaagg aggctggaat tgttacgca agtatcgcca tggcgacaga | 780 | | |
| ttatgactgc tggaaggagc acgaggaagc agtttcggtg gaccgggtct taaagaccct | 840 | | |
| gaaagaaaac gctaataaag ccaaaagctt actgctcact accatacctc agatagggtc | 900 | | |
| cacagaatgg tcagaaaccc tccataacct gaagaatatg gcccagtttt ctgttttatt | 960 | | |
| accaagacat taaagtagca tggctgccca ggagaaaaga agacattcta attccagtca | 1020 | | |
| ttttgggaat tcctgcttaa cttgaaaaaa atatgggaaa gacatgcagc tttcatgccc | 1080 | | |
| ttgcctatca aagagtatgt tgtaagaaag caagacatt gtgtgtatta gagactcctg | 1140 | | |
| aatgatttag acaacttcaa aatacagaag aaaagcaaat gactagtaaa catgtgggaa | 1200 | | |
| aaaatattac atttaaggg ggaaaaaaaa accccacca ttctcttctc ccctattaa | 1260 | | |
| atttgcaaca ataaagggtg gagggtaatc tctactttcc tatactgcca agaatgtga | 1320 | | |
| ggaagaaatg ggactctttg gttatttatt gatgcgactg taaattggta cagtatttct | 1380 | | |
| ggagggcaat ttggtaaaat gcatcaaaag acttaaaaat acggacgtcc tttggtgctg | 1440 | | |
| ggaactctac atctagcaat ttctctttaa aaccatatca gagatgcata caaagaatta | 1500 | | |
| tatataaaga agggtgttta ataatgatag ttataataat aaataattga aacaatctga | 1560 | | |
| atcccttgca attggaggta aattatgtct tagttataat ctagattgtg aatcagccaa | 1620 | | |
| ctgaaaatcc ttttttgcata tttcaatgtc ctaaaaagac acggttgctc tatatatgaa | 1680 | | |
| gtgaaaaaag gatatggtag cattttatag tactagtttt gctttaaaat gctatgtaaa | 1740 | | |
| tatacaaaaa aactagaaag aaatatatat aaccttgtta ttgtatttgg gggagggata | 1800 | | |
| ctggataat ttttatttc tttgaatctt tctgtgtctt cacattttc tacagtgaat | 1860 | | |
| ataatcaaat agtaaagggc cgtaaaaata aaagtggatt tagaaagatc cagttcttga | 1920 | | |
| aaacactgtt tctggtaatg aagcagaatt taagttggta atattaaggt gaatgtcatt | 1980 | | |
| taagggagtt acatctttat tctgctaaag aagaggatca ttgatttctg tacagtcaga | 2040 | | |

TABLE 2-continued

```
acagtacttg ggtgtgcaac agctttctga gaaaagctag gtgtataata gtttaactga  2100
aagtttaact atttaaaaga ctaaatgcac attttatggt atctgatatt ttaaaaagta  2160
atgtgagctt ctccttttta tgagttaaat tattttatac gagttggtaa tttgtgcctt  2220
ttaataaagt ggaagcttgc ttttaaaaa aaaaaaaaaa gcggaattc               2269
```

Met Glu Pro Ala Ala Gly Ser Ser Met Glu Pro Ser Ala Asp Trp Leu    SEQ. ID. NO. 3
1               5                   10                  15

Ala Thr Ala Ala Ala Arg Gly Arg Val Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Met Met Met Gly Ser Ala Arg Val Ala Glu Leu Leu Leu
50                  55                  60

Leu His Gly Ala Glu Pro Asn Cys Ala Asp Pro Ala Thr Leu Thr Arg
65                  70                  75                  80

Pro Val His Asp Ala Ala Arg Glu Gly Phe Leu Asp Thr Leu Val Val
                85                  90                  95

Leu His Arg Ala Gly Ala Arg Leu Asp Val Arg Asp Ala Trp Gly Arg
                100                 105                 110

Leu Pro Val Asp Leu Ala Glu Glu Leu Gly His Arg Asp Val Ala Arg
            115                 120                 125

Tyr Leu Arg Ala Ala Ala Gly Gly Thr Arg Gly Ser Asn His Ala Arg
    130                 135                 140

Ile Asp Ala Ala Glu Gly Pro Ser Asp Ile Pro Asp
145                 150                 155

```
cccaacctgg ggcgacttca ggtgtgccac attcgctaag tgctcggagt taatagcacc    60 SEQ. ID. NO. 4 tcctccgagc actcgctcac ggcgtcccct tgcctggaaa gataccgcgg tccctccaga   120
ggatttgagg gacagggtcg gagggggctc ttccgccagc accggaggaa gaaagaggag   180
gggctggctg gtcaccagag ggtggggcgg accgcgtgcg ctcggcggct gcggagaggg   240
ggagagcagg cagcgggcgg cggggagcag catggagccg gcggcgggga gcagcatgga   300
gccttcggct gactggctgg ccacggccgc ggcccggggt cgggtagagg aggtgcgggc   360
gctgctggag gcggggcgc tgcccaacgc accgaatagt tacggtcgga ggccgatcca   420
ggtcatgatg atgggcagcg cccgagtggc ggagctgctg ctgctccacg gcgcggagcc   480
caactgcgcc gaccccgcca ctctcacccg accgtgcac gacgctgccc gggagggctt   540
cctggacacg ctggtggtgc tgcaccgggc cggggcgcgg ctggacgtgc gcgatgcctg   600
gggccgtctg cccgtggacc tggctgagga gctgggccat cgcgatgtcg cacggtacct   660
gcgcgcggct gcggggggca ccagaggcag taaccatgcc cgcatagatg ccgcggaagg   720
tccctcagac atccccgatt gaaagaacca gagaggctct gagaaacctc gggaaactta   780
gatcatcagt caccgaaggt cctacagggc acaactgcc cccgccacaa cccacccccgc   840 tttcgtagtt ttcatttaga aaatagagct tttaaaatg tcctgccttt taacgtagat   900
atatgccttc ccccactacc gtaaatgtcc atttatatca ttttttatat attcttataa   960
aaatgtaaaa aagaaaaaca ccgcttctgc cttttcactg tgttggagtt ttctggagtg  1020
agcactcacg cccctaagcgc acattcatgt gggcatttct tgcgagcctc gcagcctccg  1080
gaagctgtcg acttcatgac aagcattttg tgaactaggg aagctcaggg gggttactgg  1140
cttctcttga gtcacactgc tagcaaatgg cagaaccaaa gctcaaataa aaataaaata  1200
attttcattc attcactc                                                 1218
```

TABLE 2-continued

| | |
|---|---|
| Met Gly Arg Gly Arg Cys Val Gly Pro Ser Leu Gln Leu Arg Gly Gln<br>1               5                        10                   15 | SEQ. ID. NO. 5 |
| Glu Trp Arg Cys Ser Pro Leu Val Pro Lys Gly Gly Ala Ala Ala Ala<br>             20                        25                        30 | |
| Glu Leu Gly Pro Gly Gly Glu Asn Met Val Arg Arg Phe Leu Val<br>        35                       40                       45 | |
| Thr Leu Arg Ile Arg Arg Ala Cys Gly Pro Pro Arg Val Arg Val Phe<br>    50                        55                        60 | |
| Val Val His Ile Pro Arg Leu Thr Gly Glu Trp Ala Ala Pro Gly Ala<br>65                      70                        75                        80 | |
| Pro Ala Ala Val Ala Leu Val Leu Met Leu Leu Arg Ser Gln Arg Leu<br>               85                        90                       95 | |
| Gly Gln Gln Pro Leu Pro Arg Arg Pro Gly His Asp Asp Gly Gln Arg<br>            100                      105                    110 | |
| Pro Ser Gly Gly Ala Ala Ala Pro Arg Arg Gly Ala Gln Leu Arg<br>        115                      120                       125 | |
| Arg Pro Arg His Ser His Pro Thr Arg Ala Arg Arg Cys Pro Gly Gly<br>    130                       135                    140 | |
| Leu Pro Gly His Ala Gly Gly Ala Ala Pro Gly Arg Gly Ala Ala Gly<br>145                  150                        155                   160 | |
| Arg Ala Arg Cys Leu Gly Pro Ser Ala Arg Gly Pro Gly<br>        165                      170 | |
| cctccctacg ggcgcctccg gcagcccttc ccgcgtgcgc agggctcaga gccgttccga    60 | SEQ. ID. NO. 6 |
| gatcttggag gtccgggtgg gagtgggggt ggggtggggg tggggtgaa ggtgggggc   120 | |
| gggcgcgctc agggaaggcg ggtgcgcgcc tgcggggcgg agatgggcag ggggcggtgc   180 | |
| gtgggtccca gtctgcagtt aagggggcag gagtggcgct gctcacctct ggtgccaaag   240 | |
| ggcggcgcag cggctgccga gctcggccct ggaggcggcg agaacatggt gcgcaggttc   300 | |
| ttggtgaccc tccggattcg gcgcgcgtgc ggcccgccgc gagtgagggt tttcgtggtt   360 | |
| cacatcccgc ggctcacggg ggagtgggca gcgccagggg cgcccgccgc tgtggccctc   420 | |
| gtgctgatgc tactgaggag ccagcgtcta gggcagcagc cgcttcctag aagaccaggt   480 | |
| catgatgatg ggcagcgccc gagtggcgga gctgctgctg ctccacggcg cggagcccaa   540 | |
| ctgcgccgac cccgccactc tcacccgacc cgtgcacgac gctgcccggg agggcttcct   600 | |
| ggacacgctg gtggtgctgc accgggccgg ggcgcggctg gacgtgcgcg atgcctgggg   660 | |
| ccgtctgccc gtggacctgg ctgaggagct gggccatcgc gatgtcgcac ggtacctgcg   720 | |
| cgcggctgcg gggggcacca gaggcagtaa ccatgcccgc atagatgccg cggaaggtcc   780 | |
| ctcagacatc cccgattgaa agaaccagag aggctctgag aaacctcggg aaacttagat   840 | |
| catcagtcac cgaaggtcct acagggccac aactgccccc gccacaaccc accccgcttt   900 | |
| cgtagttttc atttagaaaa tagagctttt aaaaatgtcc tgcctttta cgtagatata   960 | |
| tgccttcccc cactaccgta aatgtccatt tatatcattt tttatatatt cttataaaaa 1020 | |
| tgtaaaaaag aaaaacaccg cttctgcctt ttcactgtgt tggagttttc tggagtgagc 1080 | |
| actcacgccc taagcgcaca ttcatgtggg catttcttgc gagcctcgca gcctccggaa 1140 | |
| gctgtcgact tcatgacaag catttttgtga actagggaag ctcaggggg ttactggctt 1200 | |
| ctccttgagtc acactgctag caaatggcag aaccaaagct caaataaaaa taaaataatt 1260 | |
| ttcattcatt cactc 1275 | |
| Met Met Met Gly Ser Ala Arg Val Ala Glu Leu Leu Leu Leu His Gly | SEQ. ID. NO. 7 |

TABLE 2-continued

```
         1               5              10              15
Ala Glu Pro Asn Cys Ala Asp Pro Ala Thr Leu Thr Arg Pro Val His
                20                  25                  30

Asp Ala Ala Arg Glu Gly Phe Leu Asp Thr Leu Val Val Leu His Arg
                35                  40                  45

Ala Gly Ala Arg Leu Asp Val Arg Asp Ala Trp Gly Arg Leu Pro Val
            50                  55                  60

Asp Leu Ala Glu Glu Leu Gly His Arg Asp Val Ala Arg Tyr Leu Arg
65                  70                  75                  80

Ala Ala Ala Gly Gly Thr Arg Gly Ser Asn His Ala Arg Ile Asp Ala
                85                  90                  95

Ala Glu Gly Pro Ser Asp Ile Pro Asp
                100                 105
```

| | | | | |
|---|---|---|---|---|
| tgtgtggggg tctgcttggc ggtgaggggg ctctacacaa gcttcctttc cgtcatgccg | 60 | SEQ. ID. NO. 8 |
| gcccccaccc tggctctgac cattctgttc tctctggcag gtcatgatga tgggcagcgc | 120 |
| ccgagtggcg gagctgctgc tgctccacgg cgcggagccc aactgcgccg accccgccac | 180 |
| tctcacccga cccgtgcacg acgctgcccg ggagggcttc ctggacacgc tggtggtgct | 240 |
| gcaccgggcc ggggcgcggc tggacgtgcg cgatgcctgg ggccgtctgc ccgtggacct | 300 |
| ggctgaggag ctgggccatc gcgatgtcgc acggtacctg cgcgcggctg cgggggggcac | 360 |
| cagaggcagt aaccatgccc gcatagatgc cgcggaaggt ccctcagaca tccccgattg | 420 |
| aaagaaccag agaggctctg agaaacctcg ggaaacttag atcatcagtc accgaaggtc | 480 |
| ctacagggcc acaactgccc ccgccacaac ccaccccgct ttcgtagttt tcatttagaa | 540 |
| aatagagctt ttaaaaatgt cctgccttt aacgtagata taagccttcc cccactaccg | 600 |
| taaatgtcca tttatatcat tttttatata ttcttataaa aatgtaaaaa agaaaaacac | 660 |
| cgcttctgcc ttttcactgt gttggagttt tctggagtga gcactcacgc cctaagcgca | 720 |
| cattcatgtg ggcatttctt gcgagcctcg cagcctccgg aagctgtcga cttcatgaca | 780 |
| agcattttgt gaactaggga agctcagggg ggttactggc ttctcttgag tcacactgct | 840 |
| agcaaatggc agaaccaaag ctcaaataaa aataaaataa ttttcattca ttcactc | 897 |

```
Met Glu Pro Ala Ala Gly Ser Ser Met Glu Pro Ser Ala Asp Trp Leu         SEQ. ID. NO. 9
1               5                   10                  15

Ala Thr Ala Ala Ala Arg Gly Arg Val Glu Glu Val Arg Ala Leu Leu
                20                  25                  30

Glu Ala Gly Ala Leu Pro Asn Ala Pro Asn Ser Tyr Gly Arg Arg Pro
            35                  40                  45

Ile Gln Val Gly Arg Arg Ser Ala Ala Gly Ala Gly Asp Gly Gly Arg
        50                  55                  60

Leu Trp Arg Thr Lys Phe Ala Gly Glu Leu Glu Ser Gly Ser Ala Ser
65                  70                  75                  80

Ile Leu Arg Lys Lys Gly Arg Leu Pro Gly Glu Phe Ser Glu Gly Val
                85                  90                  95

Cys Asn His Arg Pro Pro Pro Gly Asp Ala Leu Gly Ala Trp Glu Thr
                100                 105                 110

Lys Glu Glu Glu
        115
```

| | | | | |
|---|---|---|---|---|
| cccaacctgg ggcgacttca ggtgtgccac attcgctaag tgctcggagt taatagcacc | 60 | SEQ. ID. NO. 10 |
| tcctccgagc actcgctcac ggcgtcccct tgcctggaaa gataccgcgg tccctccaga | 120 |
| ggatttgagg gacagggtcg gaggggggctc ttccgccagc accggaggaa gaaagaggag | 180 |

TABLE 2-continued

```
gggctggctg gtcaccagag ggtggggcgg accgcgtgcg ctcggcggct gcggagaggg    240
ggagagcagg cagcgggcgg cggggagcag catggagccg gcggcgggga gcagcatgga    300
gccggcggcg gggagcagca tggagccttc ggctgactgg ctggccacgg ccgcggcccg    360
gggtcgggta gaggaggtgc gggcgctgct ggaggcgggg gcgctgccca acgcaccgaa    420
tagttacggt cggaggccga tccagtgggg tagaaggtct gcagcgggag cagggggatgg    480
cgggcgactc tggaggacga agtttgcagg ggaattggaa tcaggtagcg cttcgattct    540
ccggaaaaag gggaggcttc ctggggagtt ttcagaaggg gtttgtaatc acagacctcc    600
tcctggcgac gccctggggg cttgggaaac caaggaagag gaatgaggag ccacgcgcgt    660
acagatctct cgaatgctga gaagatctga agggggaac atatttgtat tagatggaag    720
tcatgatgat gggcagcgcc cgagtggcgg agctgctgct gctccacggc gcggagccca    780
actgcgccga ccccgccact ctcacccgac ccgtgcacga cgctgcccgg gagggcttcc    840
tggacacgct ggtggtgctg caccgggccg gggcgcggct ggacgtgcgc gatgcctggg    900
gccgtctgcc cgtggacctg gctgaggagc tgggccatcg cgatgtcgca cggtacctgc    960
gcgcggctgc gggggggcacc agaggcagta accatgcccg catagatgcc gcggaaggtc   1020
cctcagacat ccccgattga aagaaccaga gaggctctga gaaacctcgg gaacttagat   1080
catcagtcac cgaaggtcct acagggccac aactgccccc gccacaaccc accccgcttt   1140
cgtagttttc atttagaaaa tagagctttt aaaaatgtcc tgccttttaa cgtagatata   1200
tgccttcccc cactaccgta aatgtccatt tatatcattt tttatatatt cttataaaaa   1260
tgtaaaaaag aaaaacaccg cttctgcctt ttcactgtgt tggagttttc tggagtgagc   1320
actcacgccc taagcgcaca ttcatgtggg catttcttgc gagcctcgca gcctccggaa   1380
gctgtcgact tcatgacaag catttttgtga actagggaag ctcagggggg ttactggctt   1440
ctcttgagtc acactgctag caaatggcag aaccaaagct caaataaaaa taaaataatt   1500
ttcattcatt cactc                                                    1515
ctcgcccact gcagattcct ttcccgt                                         27  SEQ. ID. NO. 11
ggcagccatg ctactttaat gtcttgg                                         27  SEQ. ID. NO. 12
```

---

I claim:

1. An MTAP-binding agent that specifically binds to human methylthioadenosine phosphorylase (MTAP) protein in an embedded, wherein said MTAP-binding agent is a monoclonal antibody produced by hybridoma cell line ATCC Accession No. PTA-5001, and wherein said biological sample is not embedded in OCT compound.

2. A hybridoma cell line that produces a monoclonal antibody that specifically binds to human MTAP protein, wherein said cell line has ATCC Accession No. PTA-5001.

3. A monoclonal antibody which specifically binds to human MTAP, wherein said monoclonal antibody is produced by a cell line ATCC Accession No. PTA-5001.

4. A kit for determining whether an embedded biological sample contains human MTAP protein comprising: (a) an MTAP-binding agent that specifically binds with an embedded human MTAP protein to form a binding complex; and (b) an indicator capable of signaling the formation of said binding complex, wherein said MTAP-binding agent is a monoclonal antibody produced by the hybridoma cell line ATCC PTA-5001.

5. Functional antigen binding fragments of a monoclonal antibody secreted by ATCC Accession No. PTA-5001.

* * * * *

UNITED STATES PATENT AND TRADEMARK OFFICE
CERTIFICATE OF CORRECTION

PATENT NO.       : 7,157,551 B2
APPLICATION NO.  : 10/779476
DATED            : January 2, 2007
INVENTOR(S)      : Lorenzo M. Leoni It is certified that error appears in the above-identified patent and that said Letters Patent is hereby corrected as shown below:

Col. 65, Claim 1, line 2
  replace "human methylthioadenosine phosphorylase (MTAP) protein"
  with --human methylthioadenosine phosphorylase (MTAP) protein, --.

Col. 65, Claim 1, line 3
  replace "in an embedded, wherein said MTAP-binding agent is a"
  with --wherein said MTAP-binding agent is a--.

Col. 65, Claim 1, line 4
  replace "monoclonal antibody produced by hybridoma cell line"
  with --monoclonal antibody produced by hybridoma cell linc--.

Col. 65, Claim 1, line 5
  replace "ATCC Accession No. PTA-5001, and wherein said biologi-"
  with --ATCC Accession No. PTA-5001.--.

Col. 65, Claim 1, line 6
  replace "cal sample is not embedded in OCT compound."
  with --blank--.

Signed and Sealed this

Twenty-seventh Day of March, 2007

JON W. DUDAS
*Director of the United States Patent and Trademark Office*